United States Patent
U. R et al.

(10) Patent No.: US 11,207,461 B2
(45) Date of Patent: Dec. 28, 2021

(54) DRUG DELIVERY SYSTEM AND METHOD FOR CONTROLLED AND CONTINUOUS DELIVERY OF DRUGS INTO THE BRAIN BY BYPASSING THE BLOOD BRAIN BARRIER

(71) Applicants: Anoop U. R, Pondicherry (IN); Kavita Verma, Pondicherry (IN)

(72) Inventors: Anoop U. R, Pondicherry (IN); Kavita Verma, Pondicherry (IN)

( * ) Notice: Subject to any disclaimer, the term of this patent is extended or adjusted under 35 U.S.C. 154(b) by 0 days.

(21) Appl. No.: 15/177,347

(22) Filed: Jun. 9, 2016

(65) Prior Publication Data

US 2017/0028127 A1 Feb. 2, 2017

(30) Foreign Application Priority Data

Jul. 30, 2015 (IN) .......................... 3904/CHE/2015
Apr. 26, 2016 (IN) ............................ 201641014398

(51) Int. Cl.
*A61M 5/142* (2006.01)
*A61C 8/00* (2006.01)
(Continued)

(52) U.S. Cl.
CPC ....... *A61M 5/14276* (2013.01); *A61C 8/0039* (2013.01); *A61C 8/0092* (2013.01);
(Continued)

(58) Field of Classification Search
CPC ....... A61C 5/70; A61C 8/0039; A61C 8/0092; A61C 8/0033; A61K 31/137;
(Continued)

(56) References Cited

U.S. PATENT DOCUMENTS 7,358,068 B2  4/2008  Vaillant et al.
7,388,079 B2  6/2008  Pardridge et al.
(Continued)

FOREIGN PATENT DOCUMENTS

GB    WO 2011098768 A1 *  8/2011  ........ A61M 5/14276

OTHER PUBLICATIONS

Joo H. Kim, A review of the maxillary sinus, Sep. 12, 2012, https://www.perioimplantadvisory.com/clinical-tips/surgical-techniques/article/16412132/a-review-of-the-maxillary-sinus#:~:text=The%20membrane%20that%20lines%20the,vascular%20connective%20tissue%20and%20periosteum (Year: 2012).*
(Continued)

*Primary Examiner* — Jenna Zhang

(57) ABSTRACT

The present invention provides devices and methods for controlled and continuous delivery of drugs into the brain by bypassing the blood brain barrier, without the need for any surgical manipulation of the brain. The respiratory mucosa in the maxillary sinus or in the nasal region is surgically accessed from the oral or maxillofacial region through a window made on the bone overlying the mucosa. The device is used to deliver drugs in a continuous and controlled manner either beneath or above the respiratory mucosa depending on the clinical requirements, drug formulation and the volume of drug used. The drug distributes into the brain from the delivery site by bypassing the blood brain barrier without causing any significant increase of the drug in the peripheral circulation. The device can be used for continuous and controlled drug delivery into the brain by bypassing the blood brain barrier for a number of medical conditions.

20 Claims, 18 Drawing Sheets

(51) Int. Cl.
*A61K 9/00* (2006.01)
*A61K 31/137* (2006.01)
*A61K 31/167* (2006.01)
*A61M 5/145* (2006.01)

(52) U.S. Cl.
CPC .......... *A61K 9/0024* (2013.01); *A61K 31/137* (2013.01); *A61K 31/167* (2013.01); *A61K 9/0004* (2013.01); *A61M 2005/14513* (2013.01); *A61M 2210/0687* (2013.01)

(58) Field of Classification Search
CPC .. A61K 31/167; A61K 9/0004; A61K 9/0024; A61M 2210/02; A61M 2210/0681; A61M 2210/0693; A61M 5/14212; A61M 5/14276
See application file for complete search history.

(56) References Cited

U.S. PATENT DOCUMENTS

| | | | |
|---|---|---|---|
| 7,510,397 B2 * | 3/2009 | Hochman | A61C 8/0033 433/172 |
| 7,618,948 B2 | 11/2009 | Kaemmerer | |
| 7,682,627 B2 | 3/2010 | Nelson et al. | |
| 7,744,879 B2 | 6/2010 | Shusta et al. | |
| 7,803,400 B2 | 9/2010 | Nelson et al. | |
| 7,905,229 B2 | 3/2011 | Giroux et al. | |
| 7,972,308 B2 | 7/2011 | Putz | |
| 7,981,417 B2 | 7/2011 | Shusta et al. | |
| 8,058,251 B2 | 11/2011 | Kaemmerer | |
| 8,119,611 B2 | 2/2012 | Kaemmerer | |
| 8,258,096 B2 | 9/2012 | Yeomans et al. | |
| 8,288,444 B2 | 10/2012 | Lilienfeld et al. | |
| 8,415,319 B2 | 4/2013 | Kaemmerer | |
| 8,497,246 B2 | 7/2013 | Pardridge et al. | |
| 8,501,691 B2 | 8/2013 | Yeomans et al. | |
| 8,622,993 B2 | 1/2014 | Frey, II et al. | |
| 8,629,114 B2 | 1/2014 | Walz | |
| 8,715,659 B2 | 5/2014 | Muruganandam et al. | |
| 8,733,342 B2 | 5/2014 | Giroux et al. | |
| 8,858,950 B2 | 10/2014 | Pardridge et al. | |
| 9,039,680 B2 * | 5/2015 | Makower | A61B 5/06 604/891.1 |
| 9,205,066 B2 | 12/2015 | Hanson, II et al. | |
| 9,211,272 B2 | 12/2015 | Frey, II et al. | |
| 9,211,273 B2 | 12/2015 | Frey, II et al. | |
| 9,216,161 B2 | 12/2015 | Frey, II et al. | |
| 9,221,867 B2 | 12/2015 | Beliveau et al. | |
| 9,249,424 B2 | 2/2016 | Wolf et al. | |
| 9,302,124 B2 | 4/2016 | Konafagu et al. | |
| 2005/0245906 A1 * | 11/2005 | Makower | G03G 5/056 604/891.1 |
| 2006/0084034 A1 * | 4/2006 | Hochman | A61C 8/0092 433/173 |
| 2010/0081111 A1 * | 4/2010 | Better | A61C 19/06 433/174 |

OTHER PUBLICATIONS

Joo H. Kim, A review of the maxillary sinus, Sep. 12, 2012, https://www.perioimplantadvisory.com/clinical-tips/surgical-techniques/article/16412132/a-review-of-the-maxillary-sinus#:~:text=The%20membrane%20that%20lines%20the,vascular%20connective%20tissue%20and%20periosteum (Year: 2012) (Year: 2012).*

* cited by examiner

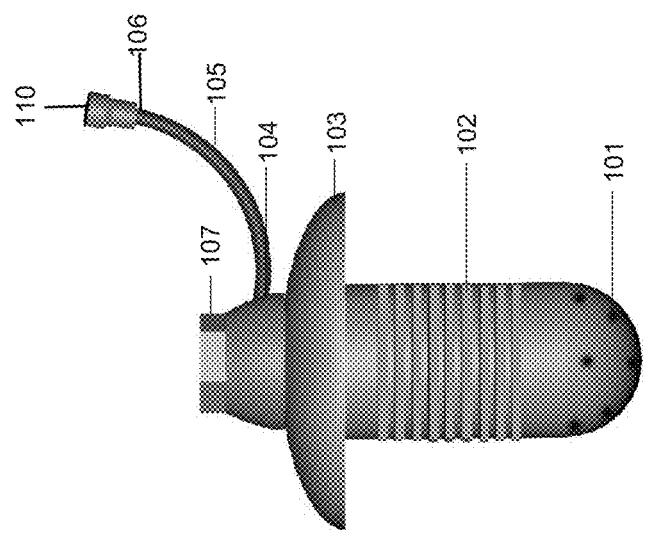
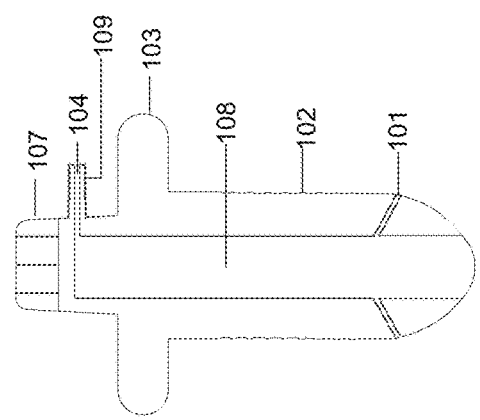
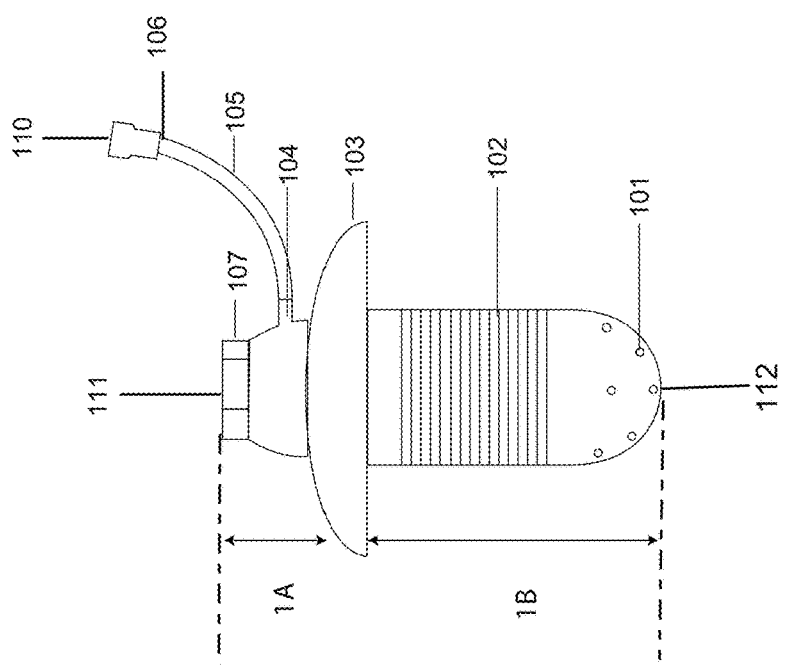
Fig-1

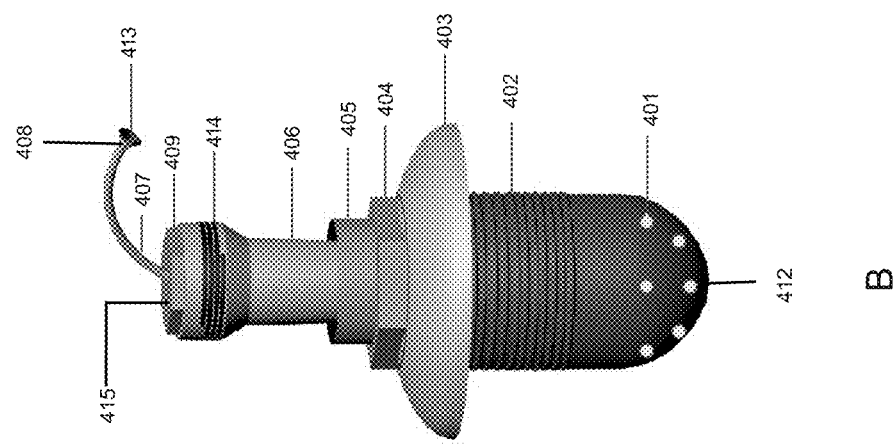
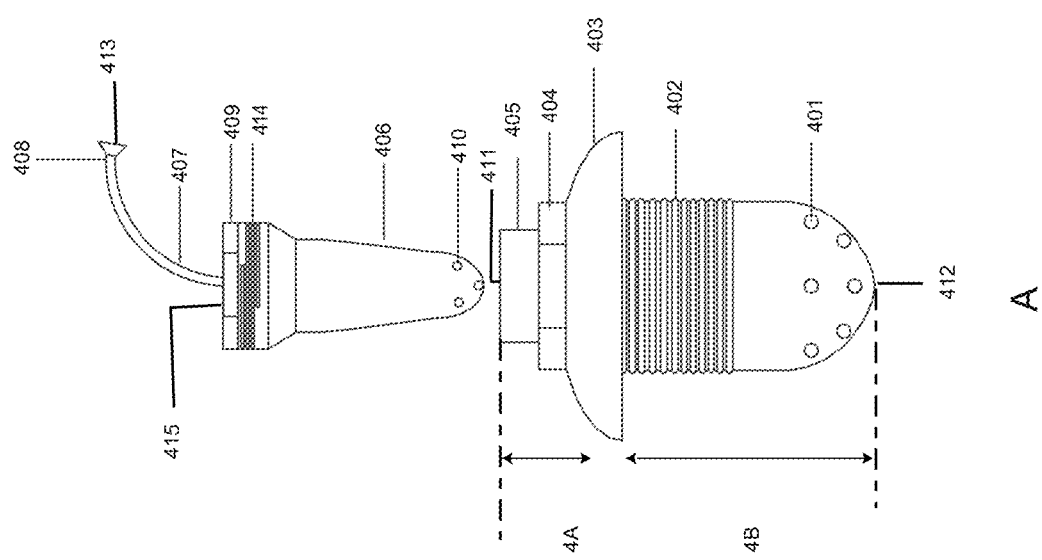
Fig-4

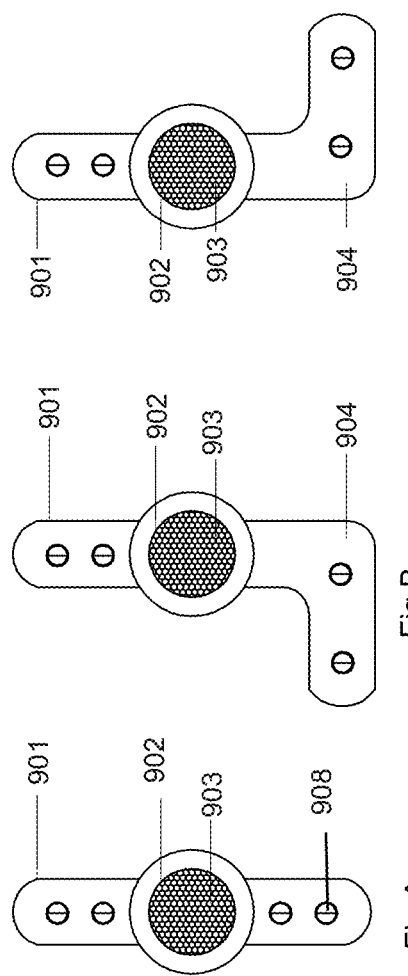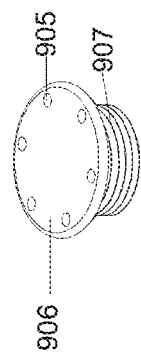
Fig-9

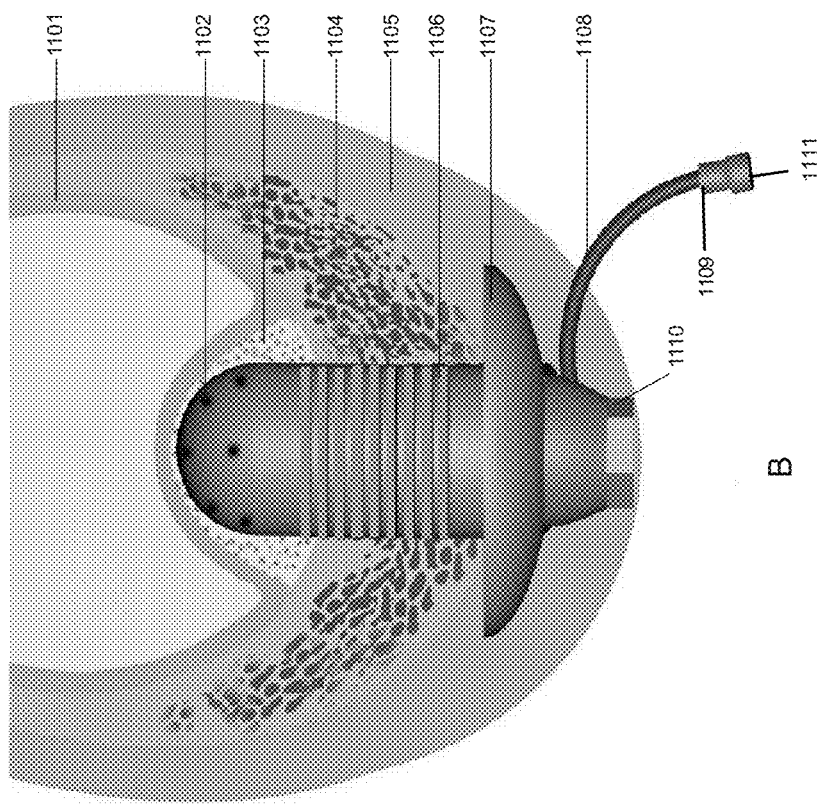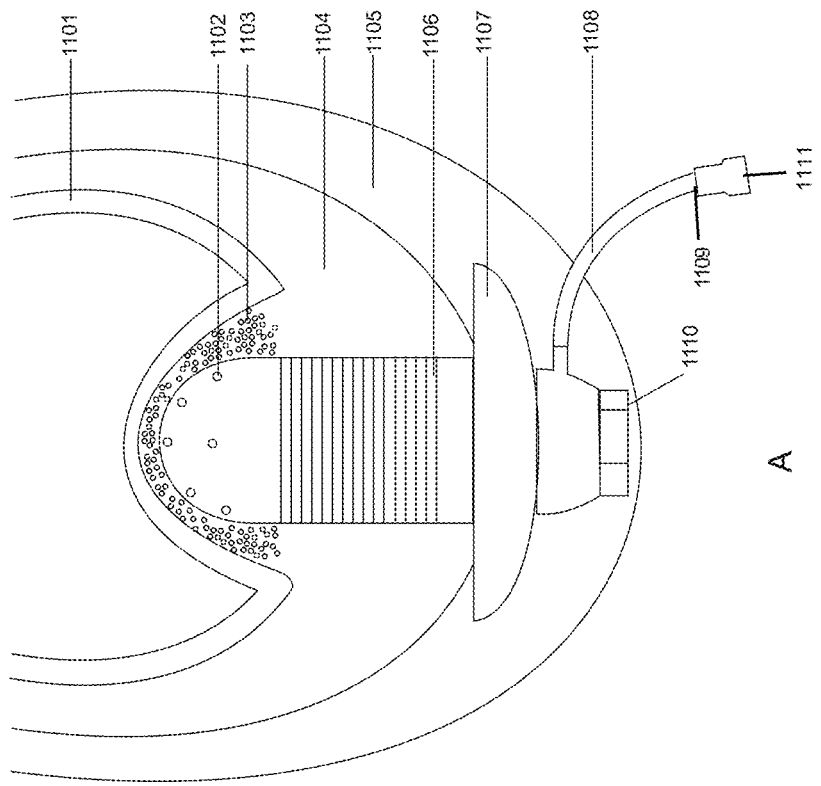
Fig-11

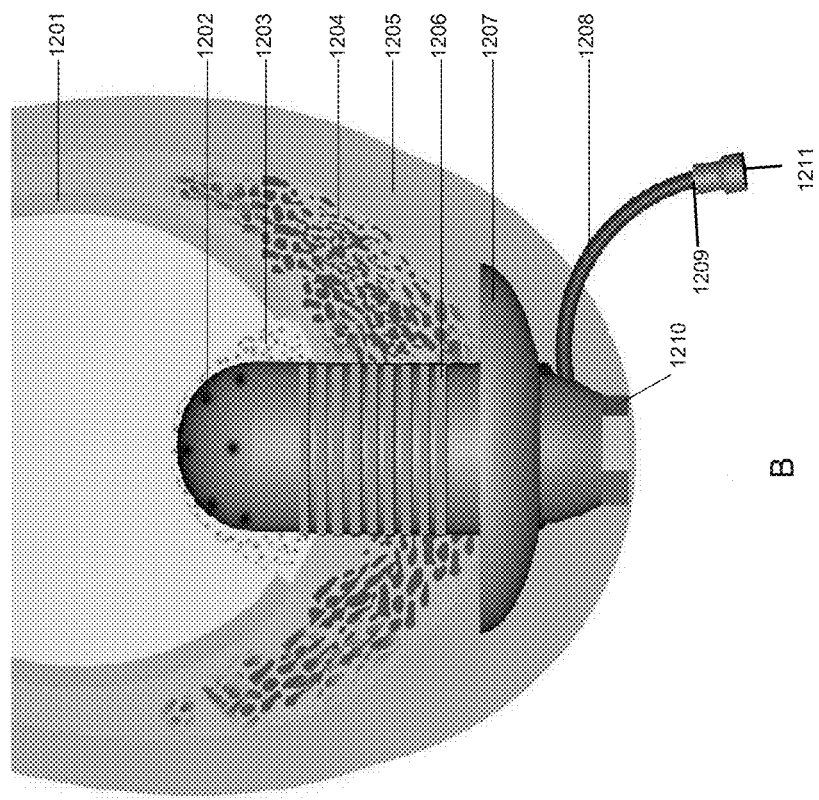
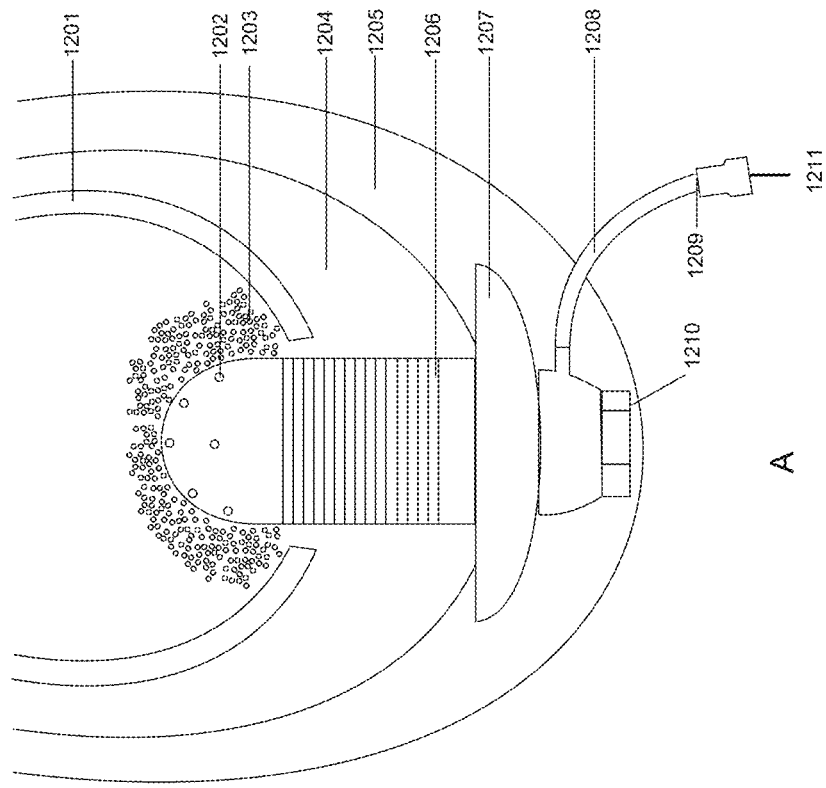
Fig-12

DRUG DELIVERY SYSTEM AND METHOD FOR CONTROLLED AND CONTINUOUS DELIVERY OF DRUGS INTO THE BRAIN BY BYPASSING THE BLOOD BRAIN BARRIER

CROSS-REFERENCE TO RELATED APPLICATIONS

This application claims foreign priority from the Indian Complete Patent Application No: 201641014398 filed in India on Apr. 26, 2016 and the Indian Complete Patent Application No: 3904/CHE/2015 filed in India on Jul. 30, 2015.

Application No: 3904/CHE/2015 filed in India on Jul. 30, 2015 is a patent of addition to the Indian Complete Patent Application No: 1430/CHE/2014 filed in India on Mar. 19, 2014. The mentioned applications are incorporated herein by reference in their entirety.

U.S.PATENT DOCUMENTS

| | | | |
|---|---|---|---|
| 9,216,161 | B2 | December 2015 | Frey, II et al |
| 9,211,273 | B2 | December 2015 | Frey, II et al |
| 9,211,272 | B2 | December 2015 | Frey, II et al |
| 9,205,066 | B2 | December 2015 | Hanson II et al |
| 8,622,993 | B2 | January 2014 | Frey, II et al. |
| 8,501,691 | B2 | August 2013 | Yeomans et al. |
| 8,258,096 | B2 | September 2012 | Yeomans et al |
| 9,249,424 | B2 | February 2016 | Wolf et al |
| 9,302,124 | B2 | April 2016 | Konafagu et al |
| 9,221,867 | B2 | December 2015 | Beliveau et al |
| 8,858,950 | B2 | October 2014 | Pardridge et al |
| 8,733,342 | B2 | May 2014 | Giroux et al |
| 8,715,659 | B2 | May 2014 | Muruganandam et al |
| 8,629,114 | B2 | January 2014 | Walz |
| 8,497,246 | B2 | July 2013 | Pardridge et al |
| 8,415,319 | B2 | April 2013 | Kaemmerer |
| 8,288,444 | B2 | October 2012 | Lilienfeld et al |
| 8,119,611 | B2 | February 2012 | Kaemmerer |
| 8,058,251 | B2 | November 2011 | Kaemmerer |
| 7,981,417 | B2 | July 2011 | Shusta et al |
| 7,972,308 | B2 | July 2011 | Putz |
| 7,905,229 | B2 | March 2011 | Giroux et al |
| 7,803,400 | B2 | September 2010 | Nelson et al |
| 7,744,879 | B2 | June 2010 | Shusta et al |
| 7,682,627 | B2 | March 2010 | Nelson et al |
| 7,618,948 | B2 | November 2009 | Kaemmerer |
| 7,388,079 | B2 | June 2008 | Pardridge et al |
| 7,358,068 | B2 | April 2008 | Vaillant et al |

FIELD OF THE INVENTION

The present invention relates to devices, systems and methods for controlled and continuous delivery of drugs into the brain by bypassing the blood brain barrier, without the need for any surgical manipulation of the brain. The drug is delivered using an implantable device either beneath or above the respiratory mucosa, by surgically creating a window on the bone overlying the respiratory mucosa and accessing the connective tissue side of the respiratory mucosal lining from the oral or maxillofacial region. The locally delivered drug can be transported through the neural, vascular or lymphatic routes or a combination of these routes and delivered into the brain by bypassing the blood brain barrier in human or animal patients. Accordingly, the present invention relates to the fields of drug delivery and medicine especially Oral and Maxillofacial Surgery, Neuroanatomy and Neurology.

BACKGROUND OF THE INVENTION

The present invention relates to implantable devices, systems and methods for controlled and continuous delivery of drugs into the brain by bypassing the blood brain barrier, without the need for any surgical manipulation of the brain The brain has good blood supply. As the brain is a highly sensitive organ, the cells lining the blood vessels in the brain are tightly arranged without any spaces between them to form a natural barrier called as the blood brain barrier. This blood brain barrier prevents entry of any foreign substance into the brain and thereby protects the brain. At the same time, it also prevents drugs present in the circulating blood from entering into the brain. Hence it is not practically possible to treat many medical conditions of the brain, even though the cause of the disease and the drug required for the treatment are known, because of the simple reason that the drug cannot enter the brain.

In the recent years, more information about the central nervous system and blood brain barrier have been unraveled using advanced molecular and imaging techniques. This has led to identification of newer therapeutic targets for drugs at the molecular level. New drugs have also been developed which can act on these molecular targets. Though in vitro studies and pre-clinical studies are positive for these drugs, they show high failure rate when administered in humans. This is mainly because the drugs are not able to enter the brain in the required therapeutic concentration to produce the pharmacologic effects. In fact, 98% of small drugs and almost 100% of large drugs are not able to cross the barrier. Hence there is a need for an effective drug delivery route which can deliver the drug into the brain at the right concentration in a continuous but controlled manner.

The methods available today for delivering drugs directly into the brain are mostly invasive. The methods include placement of micro-catheters or implants into the brain or use of various techniques to open the blood brain barrier. These techniques however make the brain also prone to infection as the brain gets exposed to the external environment. Advancement in the field of proteomics and genomics has led to discovery of therapeutic targets at the level of molecules or genes in the brain, leading to development of newer drugs. But these drugs also get destroyed when given orally. Hence alternative routes for drug delivery are the need of the hour.

Recent studies have shown that the nasal route can be used as anon-invasive route to deliver the drugs directly to the brain. But this route has limitations because controlled and continuous delivery of drugs at predetermined rates has not yet been achieved. The drugs also have to withstand mucociliary clearance, local enzymatic degradation and cross the epithelial layer before they reach the underlying connective tissue for further absorption. Hence only a smaller quantity of the total drug that is delivered, is finally absorbed. Drugs modified for endogenous transport mediated delivery across the blood brain barrier, using the naturally occurring molecular transport mechanisms at the endothelial cell have been developed for a few medical conditions. Yet the concentration of the drug delivered across the blood brain barrier using this technique is not predictable. Protein mediated drug delivery and viral mediated gene therapy can induce immune mediated complications. Systemic routes like intra venous or intra-arterial need high concentration of the drug. Moreover, intra-arterial route results in severe complications. Therefore, an effective alternative route which can deliver drugs into the brain in a controlled and continuous manner, for a long period of time, without any complications or discomfort to the patient holds immense potential.

Trigeminal nerve supplies the nasal respiratory mucosa and the maxillary sinuses and relays at the nuclei in the brainstem. Cerebrospinal fluid has also been found to drain through nasal lymphatics. The nasal lymphatic channels are free of valves and can hence be used for drug delivery. Blood vessels in the nasal and maxillary sinus region can also transfer the drugs to the brain. The veins from the maxillary sinus and the nasal region drain into the pterygoid venous plexus which is further connected to the cavernous sinus. Therefore, the drugs delivered locally in these regions can drain into the pterygoid venous plexus and be further transferred into the cavernous sinus. The drugs can then enter the cerebral circulation at higher concentration without causing systemic toxicity either through the counter current mechanism at the cavernous sinus or through the perivascular pathways. Hence the drug delivered locally beneath the respiratory mucosa, can be transported from the nasal and maxillary sinus region through the neural, lymphatic and the vascular routes into the brain by bypassing the blood brain barrier.

The air circulation in the maxillary sinus is unique. The maxillary sinus fills with air during expiration and is emptied of air during inspiration. Hence a drug delivered into the maxillary sinus by perforating the sinus lining mucosa from the connective tissue side can be easily inhaled when the air inside the maxillary sinus is emptied during inspiration. The drug can further come in contact with the nasal respiratory and olfactory mucosa for absorption. Also, the mucus on the maxillary sinus lining mucosa is moved towards the ostium opening and into the middle meatus of nose because of the muco-ciliary action. Hence the drug delivered on the maxillary sinus lining mucosa can also be transported by the muco-ciliary action through the ostial opening into the middle meatus and onto the nasal respiratory mucosa. Because of the increased retention time of the drug on the mucosal surface, higher quantity of the drug can be inhaled and be deposited on the nasal respiratory and olfactory mucosa for further absorption into the underlying connective tissue.

Goblet cells in the maxillary sinus lining mucosa secrete mucus. Drugs can be engineered for uptake from the connective tissue into the goblet cells, for further secretion along with mucus by the goblet cells. This can result in mucus loaded with high concentration of drug molecule for inhalation. The inhaled drug can be deposited on the nasal respiratory mucosa and olfactory mucosa for further absorption.

It therefore would be desirable to deliver drugs into the brain using a device without any need for surgical manipulation of the brain. It would further be desirable to provide a device which can be surgically implanted with its delivery tip located either beneath or above the respiratory mucosa, by surgically creating a window on the bone overlying the respiratory mucosa and accessing the connective tissue side of the respiratory mucosal lining from the oral or maxillofacial region. It would also be desirable to deliver the drug in a controlled and continuous manner by connecting the device to an external drug infusion pump. The drug from the respiratory mucosa can be transported through the neural, vascular, lymphatic, inhalation or a combination of all these routes and delivered into the brain by bypassing the blood brain barrier and without causing any systemic toxicity.

SUMMARY OF THE INVENTION

The present invention provides a drug delivery system for delivering drugs into the brain, by bypassing the blood brain barrier. The drug delivery system comprises an implantable hollow device made of titanium or any other biocompatible material, that is placed into the bone overlying the respiratory mucosa of the maxillary sinus or the nasal cavity and a drug delivery tubing made of a biocompatible material that transfers therapeutic agents from an external drug reservoir into the central lumen of the implantable hollow device. An external drug infusion pump is used for providing continuous and controlled delivery of therapeutic agents from the external drug reservoir into the central lumen of the implantable hollow device.

A method of drug delivery into the brain by bypassing the blood brain barrier using the drug delivery system is described. The device is used to deposit the drug beneath the respiratory mucosa, by surgically creating a bone window on the overlying bone and accessing the connective tissue side of the respiratory mucosal lining from the oral or maxillofacial region. The drug delivered locally beneath the respiratory mucosa, can be transported from the nasal and maxillary sinus region through the neural, lymphatic and the vascular routes into the brain by bypassing the blood brain barrier.

Another method of drug delivery into the brain by bypassing the blood brain barrier is described wherein the tip of the drug delivery device is placed into the maxillary sinus and above the level of the epithelial lining of the respiratory mucosa, by surgically creating a bone window on the overlying bone and perforating the underlying respiratory mucosa from the connective tissue side. The mucosa is perforated by removing the circumscribed bone with the trephine drill along with the underlying respiratory mucosa attached to the bone. The drug delivered into the maxillary sinus can be easily inhaled during inspiration and can be deposited at the nasal respiratory and olfactory mucosa for further absorption. The drug can also be transported through the ostial opening into the middle meatus and onto the nasal respiratory mucosa by muco-ciliary action. This results in increased retention time of the drug on the mucosal surface and so higher quantity of the drug can be absorbed into the connective tissue vasculature at the respiratory mucosa and the olfactory mucosa.

Drug molecules that are engineered for uptake into the goblet cells of the maxillary sinus lining epithelium, from the underlying connective tissue for further secretion by the goblet cells along with mucus are described. This can result in mucus loaded with high concentration of drug molecule for inhalation, which can be deposited on the nasal respiratory mucosa and the olfactory mucosa for further absorption.

Drug molecules that are engineered for affinity to specific sites of the brain are described. This provides the required concentration of the drug in the targeted anatomical site in the brain.

The present invention is illustrated by the accompanying drawings of various embodiments and the detailed description given below. The drawings are not to scale. The detailed description and drawings merely depict exemplary embodiments of the present invention, for explanation and understanding and therefore should not be taken to limit the scope of the invention to the specific embodiments. Accordingly, the scope of the invention is to be defined solely by the appended claims and equivalents thereof. It will be appreciated that the components of the present invention illustrated in the drawings could be arranged, sized and designed in a number of different configurations.

Implantable devices and methods for controlled and continuous drug delivery into the brain by bypassing the blood brain barrier for a number of medical conditions including Parkinson's. Alzheimer, Pain Management, Epilepsy and Drug Addiction are provided.

BRIEF DESCRIPTION OF THE DRAWINGS

FIG. 1 shows the isometric side view (A), longitudinal sectional view (B) and three-dimensional view (C) of the single unit device.

FIG. 4 shows the isometric side view (A) and three-dimensional view (B) of a multiunit device comprising a device with a central tubular inlet with internal threads (405) at the cervical third and a drug delivery assembly (406) with external threads (414) at its cervical part.

FIG. 9 shows a mini plate (A, B, C) with a central reservoir dial (902) comprising internal threads and a porous apical wall (903) which is closed with a cap (D) with external threads (907).

FIG. 11 shows the device with the porous apical wall (1102) located beneath the respiratory mucosa (1101).

FIG. 12 shows the device with the porous apical wall (1202) located above the level of the respiratory mucosa (1201).

DETAILED DESCRIPTION OF THE INVENTION

Figure 2:
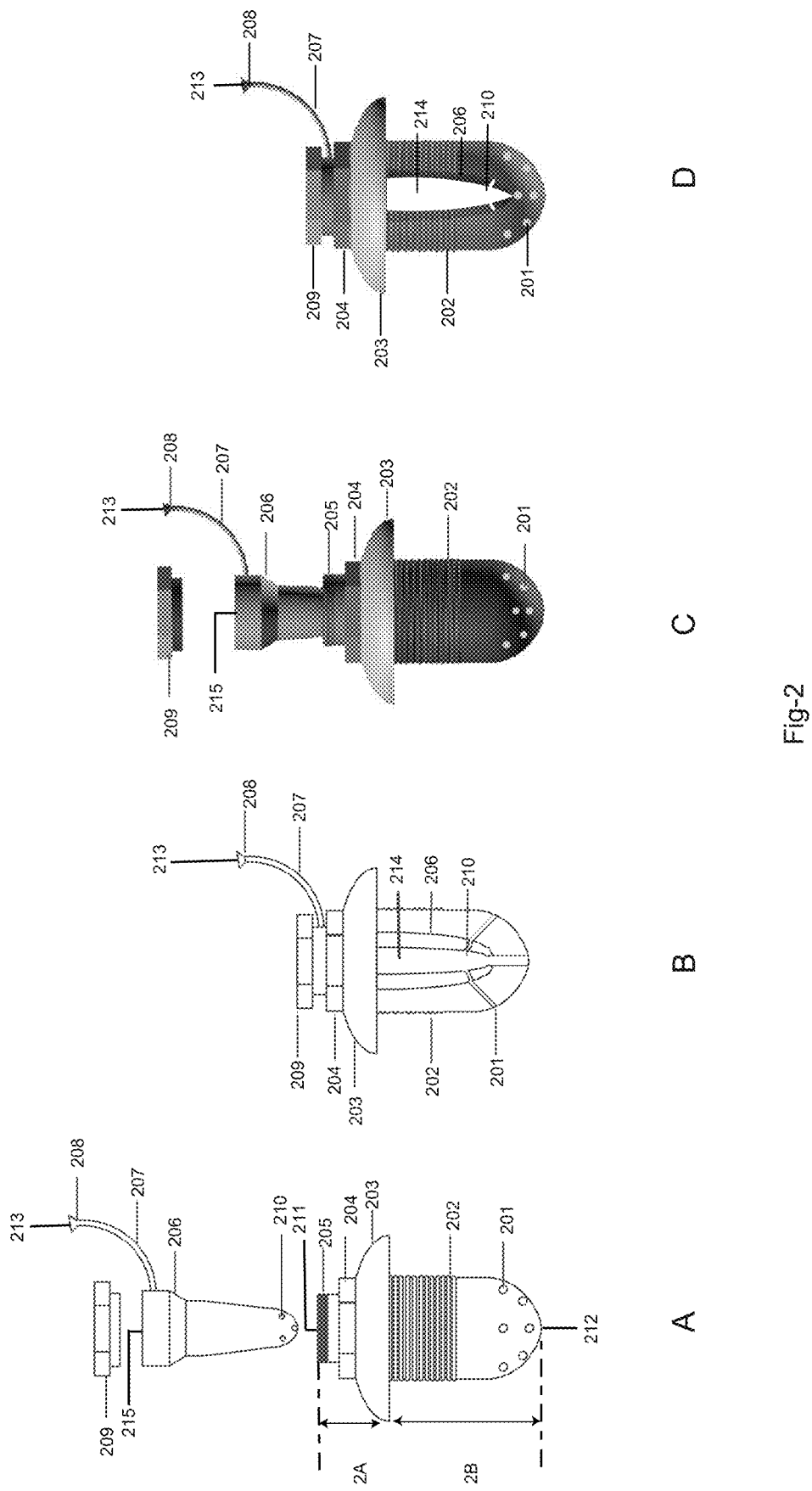
FIG. 2 shows the isometric side view (A), longitudinal sectional view (B), and three-dimensional view (C, D), of a multi-unit device comprising a device with a central tubular inlet with external threads (205), a drug delivery assembly (206) and a retention cap (209).

The following detailed description of exemplary embodiments of the invention makes reference to the accompanying drawings which form a part hereof. The exemplary embodiments of the invention and the method to practice the invention are hereby illustrated in the accompanying drawings. Though the exemplary embodiments are described in sufficient detail to enable those skilled in the art to practice the invention, it should be appreciated that various modifications and configurations to the present invention Accordingly, the scope of the invention is to be defined solely by the appended claims and equivalents thereof.

It must be appreciated that, in the specification and in the appended claims, the singular forms "a," "an" and "the" refer to plural forms unless the context clearly dictates otherwise. Therefore, reference to "the surgical placement" refers to one or more steps and "a therapeutic agent" refers to one or more therapeutic agents.

Definitions

In describing and claiming the invention, the following terminology will be used to denote the definitions set forth below As used herein, "first end," "coronal end," "top end" and "upper end" (111,211,311,411) may be used interchangeably to refer to the end of the device that is present above the level of the ring and remains above the bone when implanted into the surgical site.

As used herein, "first part," "coronal part," "top part" and "upper part" (1A,2A,3A,4A) may be used interchangeably to refer to the part of the body of the device that projects above the level of the ring and remains above the bone when implanted into the surgical site.

As used herein. "second end," "apical end," "bottom end" and "lower end" (112,212,312,412) may be used interchangeably to refer to the end of the device that is present below the level of the ring and remains below the bone, in contact with the respiratory mucosa when implanted into the surgical site.

As used herein, "second part," "caudal part" "bottom part" and "lower part" (1B,2B,3B,4B) may be used interchangeably to refer to the part of the body of the device that projects below the level of the ring and remains within the bone when implanted into the surgical site As used herein "proximal part," and "mesial part" may be used interchangeably to refer to the part which is nearest to the point of reference or the part that is closest to the median plane of the device.

As used herein "distal part" refers to the part which is away from the point of reference or the part that is farther away from the median plane of the device.

As used herein "cervical third" refers to the upper third part of the lower part of the body of the device that extends from below the level of the ring, or to the upper third part of the body of the device in the form of a dental implant, wherein the body is divided horizontally by imaginary lines into three equal parts As used herein "middle third" refers to the middle third part of the lower part of the body of the device that extends from below the level of the ring, or to the middle third part of the body of the device in the form of a dental implant, wherein the body is divided horizontally by imaginary lines into three equal parts As used herein "apical third" refers to the lower third part of the lower part of the body of the device that extends from below the level of the ring, or to the lower third part of the body of the device in the form of a dental implant, wherein the body is divided horizontally by imaginary lines into three equal parts.

As used herein, "superior surface" may be used to refer to the upper surface of a flat or similar shaped embodiment.

As used herein, "inferior surface" may be used to refer to the lower surface of a flat or similar shaped embodiment.

As used herein. "inlet," and "tubular opening" may be used interchangeably to refer to the part of the device that is tubular in shape and is located on the upper part of the device, to which a drug delivery tubing can be attached for drug delivery into the device.

As used herein, "central lumen", and "central vent" may be used interchangeably to refer to the central hollow space within the body of the device, which further opens to the outside through the inlet on the coronal end and through multiple holes at the apical end.

As used herein, "apical wall" may be used to refer to the wall comprising the rounded apical end and part of the apical third of the lower part of the device.

As used herein, "slot" and "cleft" may be used interchangeably to refer to a vertical opening in the upper end of the inlet into which the drug delivery tubing is placed.

As used herein, "drug delivery assembly" refers to a hollow tubing comprising a vertical part that is placed into the device and a lateral tube extending from the side of the vertical part, wherein the mesial part of the tube is placed into the slot of an inlet present on the device.

As used herein, "intra implant part" refers to the vertical part of the drug delivery assembly that is placed into the device.

As used herein, "external drug delivery tubing" or "external tubing" may be used interchangeably to refer to the tube extending from the side of the vertical part of the drug delivery assembly that is placed into the slot of an inlet of the device.

As used herein, "tubing," and "drug delivery tubing" may be used interchangeably to refer to the tube attached to the inlet of the device.

As used herein, "intra oral part" refers to the part projecting into or the part facing the oral cavity.

As used herein, "intra bony part" refers to the part within the bone or below the level of the bone.

As used herein "intra-pulpal part" refers to the part that is within the pulp cavity of the tooth.

As used herein, "osseointegration" refers to the process of bone formation around the implant and on the surface of the device facing the bone.

As used herein, "abutment," refers to the removable part that can be placed into the device which is in the form of a dental implant. It can be in the form of a drug delivery assembly or can comprise an internal a drug reservoir with an in-built internal drug infusion pump.

As used herein "external involute spline" refers to an involute spline whose tip surface is located on the external surface of the body of the embodiment.

As used herein "internal involute spline" refers to an involute spline whose tip surface is located on the internal surface of the body of the embodiment.

As used herein, "claw," refers to the curved part of the tool that is used for holding a retention cap by its margin.

As used herein, "shaft," refers to the part of the instrument, present between the head and the handle.

As used herein, "reservoir," and "drug reservoir" may be used interchangeably to refer to a body comprising a cavity that holds a therapeutic agent. The therapeutic agent may be in a form in which it can be easily transferred from the reservoir into the device in a controlled and continuous manner. As used herein, "external drug reservoir," refers to a reservoir which is present outside the patient. It is connected to the device in the patient by a tubing whenever drug delivery is required.

As used herein, "internal drug reservoir," refers to a reservoir which is present within the implant. It may be in the form of a cavity within the abutment.

As used herein, "infusion pump," and "drug infusion pump" may be used interchangeably to refer to the device that can move the therapeutic agent from the reservoir to the inside of the device in a controlled and continuous manner.

As used herein, "therapeutic agent," and "drug" may be used interchangeably to refer to an agent or substance that can produce a pharmacologic effect in a human or animal patient when administered into the patient or that is useful as a diagnostic agent when administered in a patient.

The surgical steps claimed in the methods, can be executed by changing the order of steps or by avoiding some steps depending on the clinical requirements and are not limited to the order presented in the claims unless otherwise stated. Accordingly, the scope of the invention should be determined by the appended claims and their legal equivalents, rather than by the descriptions and examples given herein.

Drug Delivery Device:

In the preferred embodiment, the single unit implantable device (FIG. 1: A, B, C) has a hollow, cylindrical or tapered body which is closed at both the ends. The body comprises an upper, first part (1A) and a lower, second part (1B). with a barrier ring (103) located on the outer surface of the body between the two parts. The outer surface of the second part (1B) of the body of the device that is located below the circular barrier ring comprises threads (102) from the cervical third to the middle third. The apical part is smooth and has a plurality of holes (101) through the apical wall. The holes are configured in the form of macro-holes, micro-holes, nano-holes or a combination. A central lumen (108) is present within the body. The central lumen extends from the first part (1A) of the body to the second part of the body (13) and is defined by the internal wall of the device. The porous apical wall is placed either in contact (FIG. 11) with the connective tissue of the respiratory mucosa or above the level of the epithelial lining (FIG. 12) of the respiratory mucosa. The first closed (111) end of the device has an external hex (107) for holding and placement of the device. A drug delivery inlet (104) is present below the level of the external hex on the side of the first part (1A) of the body of the device for the attachment of a drug delivery tubing (105). The inlet (104) is configured in the form of an opening with or without internal threads or in the form of a tubular projection. The tubular inlet comprises of either a smooth external surface or a surface with external or internal threads. The tubular inlet is either perpendicular to the external surface of the body of the device or angulated towards the coronal end. The inlet (104) opens into the central lumen (108) present within the body of the device. The central lumen (108) further opens to the exterior through the plurality of holes (101) at the apical wall. A drug delivery tubing (105) is removably secured to the inlet (104). Whenever required, the free, second open end (106) of the drug delivery tubing is connected to a drug infusion source comprising an external drug reservoir attached to an external a drug infusion pump for controlled drug delivery. The circular barrier ring (103) is present below the inlet and prevents the accidental inward displacement of the device into the maxillary sinus or into the nasal cavity. The device is made of titanium or any other biocompatible material. The tubing is also made of a resilient and biocompatible material that allows good soft tissue adaptation. The device is manufactured in varying diameters and lengths to suit the different clinical requirements.

The device delivers one or more drugs in a controlled and continuous manner, locally at the surgical site in the respiratory mucosal region. The drugs can then be transported by neural, vascular, lymphatic or inhalation routes or by a combination of these routes into the brain by bypassing the blood brain barrier.

Exemplary, non-limiting embodiments of the brain drug delivery device are illustrated in FIG. 1-18. These figures illustrate variations of the drug delivery device and the methods for use.

The preferred embodiment is illustrated in FIG. 1. Referring to FIG. 1 Fig: A refers to the isometric side view of the single unit device. 101 refers to a plurality of holes through the apical wall of the body of the device that is placed either beneath or above the respiratory mucosa. 102 refers to the threads on the outer surface of the device located at the cervical third and middle third of the second part of the body of the device. 103 refers to the barrier ring that prevents the unintentional inward displacement of the implant into the maxillary sinus or the nasal cavity. 104 refers to the inlet. 105 refers to the drug delivery tubing. The first open end of the tubing is either friction fit or threaded onto or into the inlet (104). The second open end (106) of the tubing is free. 110 refers to a temporary cap removably coupled to the free second open end of the drug delivery tubing. The second open end can be placed in the buccal sulcus overlying the mucosa, in the buccal gingival sulcus or in the palatal gingival sulcus. 107 refers to the external hex of the device which removably secures to a holding device and thereby assists in holding and placement of the device into the surgical site. 111 refers to the first closed end of the device. 112 refers to the second end of the device. 1A refers to the first part of the device. 1B. refers to the second part of the device Fig: B refers to the longitudinal sectional view of the device. 101 refers to a plurality of holes through the apical wall of the device. 102 refers to the threads on the outer surface of the second part of the device. 103 refers to the barrier ring. 104 refers to the inlet to which the drug delivery tubing is connected. 107 refers to the external hex. 108 refers to the central lumen. 109 refers to the external threads on the inlet. Fig: C refers to the 3D rendered view of Fig: A.

An alternative embodiment is illustrated in FIG. 2. The alternative embodiment is a multiunit device comprising an inlet (205) located centrally at the first end (211) of the body of the device. The inlet further comprises external threads at its cervical third and a vertical slot extending from its tip to its middle third. The drug delivery assembly comprises an intra implant part (206) and an external tubing (207). The intra implant part is tapering in shape and comprises a central lumen (214) within the body and a plurality of holes (210) through the apical wall. The external tubing (207) is tubular in shape and comprises a central lumen. It extends from the side of the intra-implant part. The central lumen of the intra implant part and that of the external tubing are continuous with each other. When the intra-implant part is inserted into the central lumen of the device, the mesial part of the external tubing removably adapts to the vertical slot on the side of the inlet. A cap (209) is threaded onto the external threads on the inlet of the device. The cap covers the slot and extends till the surface of the tubing. The cap retains the intra-implant part within the device. An external hex (204) is present below the inlet. It helps in holding and placing the device. A circular ring (203) is present below the external hex. It prevents the accidental inward displacement of the device into the maxillary sinus or into the nasal cavity. Referring to FIG. 2, Fig: A refers to an isometric side view of a multi-unit drug delivery device. 211 refers to the first open end of the device. 212 refers to the second end of the device. 2A refers to the first part of the device. 2B refers to the second part of the device. 201 refers to the plurality of holes through the apical wall of the body of the device that is placed either beneath or above the respiratory mucosa. 202 refers to the threads on the outer surface of the device located at the cervical third and middle third of the second part of the device body. 203. Refers to the barrier ring. 204. Refers to the external hex. 205 Refers to the tubular inlet with external threads. 206 Refers to the intra implant part of the drug delivery assembly. (215) refers to the first closed end of the intra-implant part of the drug delivery assembly. 210 refers to the plurality of holes at the apical wall of the intra implant part of the drug delivery assembly. 207 Refers to the external tubing of the drug delivery assembly. 208 refers to the open end of the external tubing of the drug delivery assembly 213 Refers to the cap removably coupled to the open end of the external tubing of the drug delivery assembly 209. Refers to the cap with internal threads that can be threaded onto the inlet of the device. It retains the intra implant part of the drug delivery assembly within the device. Fig: B is a longitudinal sectional view of the second part of the device and the components comprised within. 201. Refers to the porous apical wall of the device. 202. Refers to the external threads on the body of the device 203. Refers to the barrier ring. 204. Refers to the external hex. 206. Refers to the intra implant part of the drug delivery assembly with a central lumen (214) and porous tip. 207. Refers to the external tubing of the drug delivery assembly. 208 refers to the open end of the external tubing of the drug delivery assembly 213 Refers to the cap removably coupled to the open end of the external tubing of the drug delivery assembly 209. Refers to the cap with internal threads that is threaded onto the inlet of the device. It retains the intra implant part of the drug delivery assembly within the device. 210. Refers to the porous apical wall of the intra implant part of the drug delivery assembly within the device. Fig: C is a 3D rendered view of Fig A. Fig: D is a 3D rendered view of Fig B.

Figure 3:
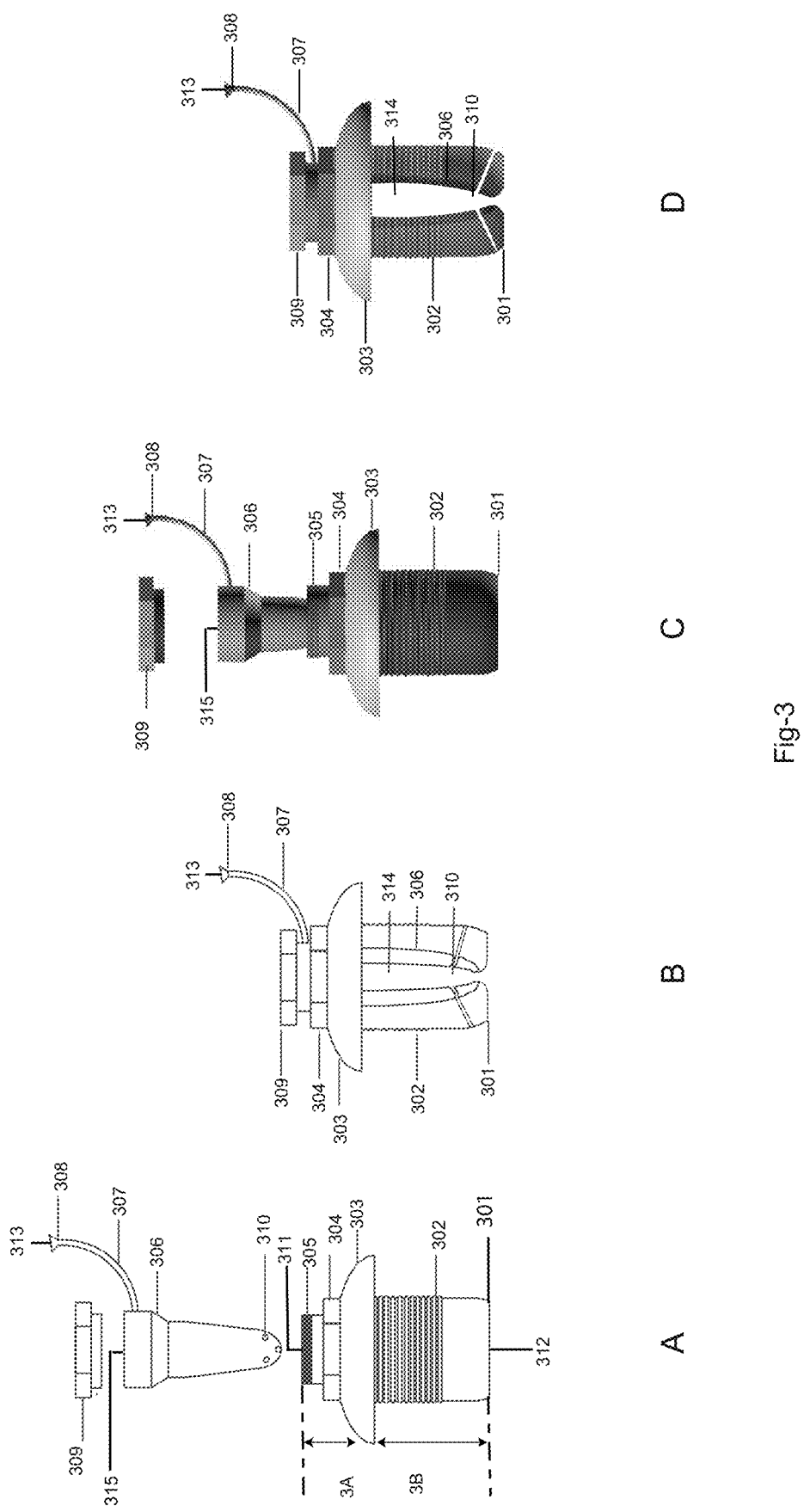
FIG. 3 shows the isometric side view (A), longitudinal sectional view (B) and three-dimensional view (C, D) of a multiunit device comprising a device with a completely open second end (312) with smooth and rounded margin (301).

Another alternative embodiment is illustrated in FIG. 3. The alternative embodiment is a multiunit device comprising a completely open second end (312) with a beveled and outwardly flaring internal wall that forms a smooth and rounded margin (301) and a tubular inlet (305) located centrally at the first end (311) of the body of the device. The inlet further comprises external threads at its cervical third and a vertical slot extending from its tip to its middle third. The drug delivery assembly comprises an intra implant part (306) and an external tubing (307). The intra implant part is tapering in shape and comprises a central lumen (314) within the body and a plurality of holes (310) through the apical wall. The external drug delivery tubing (307) is tubular in shape and comprises a central lumen. It extends from the side of the intra-implant part. The central lumen of the intra implant part and that of the external drug delivery tubing are continuous with each other. When the intra-implant part is inserted into the central lumen of the device, the mesial part of the external tubing removably adapts to the vertical slot on the side of the inlet. The tip of the intra-implant part (30) is positioned at the apical opening of the central lumen and is located below the level of the rounded apical margin (301). A cap (309) is threaded onto the external threads on the inlet of the device. The cap covers the slot and extends till the surface of the tubing. The cap retains the intra-implant part within the device. An external hex (304) is present below the inlet. It helps in holding and placing the device. A circular ring (303) is present below the external hex. It prevents the accidental inward displacement of the device into the maxillary sinus or into the nasal cavity. Referring to FIG. 3, Fig: A refers to an isometric side view of a multi-unit implant with a completely open apex 311 refers to the first open end of the device. 312 refers to the second open end of the device. 3A refers to the first part of the device. 3B refers to the second part of the device. 301. Refers to the smooth and rounded margins at the completely open second end. 302. Refers to the external threads 303. Refers to the barrier ring. 304. Refers to the external hex. 305 Refers to the tubular inlet with external threads. 306 Refers to the intra implant part of the drug delivery assembly. (315) refers to the first closed end of the intra-implant part of the drug delivery assembly. 310 refers to the plurality of holes at the apical wall of the intra implant part of the drug delivery assembly. 307 Refers to the external tubing of the drug delivery assembly. 308 refers to the open end of the external tubing of the drug delivery assembly. 313 Refers to the cap removably coupled to the open end of the external tubing of the drug delivery assembly. 309. Refers to the cap with internal threads that can be threaded onto the inlet of the device. It retains the intra implant part of the drug delivery assembly within the device. Fig: B is a longitudinal sectional view of the second part of the implant body and the components comprised within. 301. Refers to the smooth and rounded margin at the completely open second end of the device 302. Refers to the external threads on the body of the device. 303. Refers to the barrier ring. 304. Refers to the external hex. 306. Refers to the intra implant part of the drug delivery assembly with a central lumen (314) and a porous apical tip which is placed below the level of the margin of the second open end. 307. Refers to the external tubing of the drug delivery assembly. 308. refers to the open end of the external tubing of the drug delivery assembly. 313 Refers to the cap at the open end of the external tubing of the drug delivery assembly. 309. Refers to the cap with internal threads that is threaded onto the inlet of the device. It retains the intra implant part of the drug delivery assembly within the device. 310. Refers to the porous apical wall of the intra implant part of the drug delivery assembly within the device. Fig: C is a 3D rendered view of Fig A. Fig: D is a 3D rendered view of Fig B.

An alternative embodiment is illustrated in FIG. 4. The alternative embodiment is a multi-unit implantable device with a hollow cylindrical body comprising an upper, first open end (411) and a closed second or apical end (412). The second or apical end is rounded with a plurality of holes (401) through the apical wall and the first or upper end comprises an inlet 405) with internal threads at its cervical third. A barrier ring (403) is present between the inlet (405) and the plurality of the holes (401) on the external surface of the body of the device and comprises a convex and smooth upper surface and a flat and smooth undersurface facing the bone. The external surface of the first or upper part (4A) of the body further comprises an external hex (404) disposed between the drug delivery inlet (405) and the barrier ring (403). A central lumen is present within the body of the device and is defined by the tapering internal wall of the body of the device. The central lumen extends from the inlet (405) at the upper, first end to the plurality of holes (401) in the apical wall. Threads (402) are present on the external surface of the second or lower part (4A) of the body at the cervical third, below the level of the ring. The drug delivery assembly comprises a tapered intra-implant part (46 with external threads (414) at its upper part and an external drug delivery tubing (407) attached to the first end (415) of the intra-implant part. The intra-implant part (406) of the drug delivery assembly is threaded into the inlet (405) of the device wherein the external walls of the intra implant part adapt tightly to the internal walls of the device except at the apical third. A space is present at the apical third between the internal wall of the device and the external wall of the intra-implant part, wherein the drug is initially delivered. The drug further moves out through the holes (401) at the apical wall of the device. Referring to FIG. 4, Fig: A refers to an isometric side view of a multi-unit device with the tubular central inlet with internal threads at the first end. 411 refers to the first open end of the device. 412 refers to the second end of the device. 4A refers to the first part of the device. 4B refers to the second part of the device. 401. Refers to the porous apical wall of the device. 402. Refers to the external threads 403. Refers to the barrier ring. 404. Refers to the external hex. 405 Refers to the tubular inlet with internal threads. 406 Refers to the intra implant part of the drug delivery assembly. (415) refers to the first end of the intra implant part of the drug delivery assembly. 407 Refers to the external tubing of the drug delivery assembly. 408 refers to the open end of the external tubing of the drug delivery assembly. 413 Refers to the cap removably coupled to the open end of the external tubing of the drug delivery assembly. 409 refers to the external hex at the first end of the intra implant part 410. Refers to the porous apical wall of the intra implant part of the drug delivery assembly. 414 Refers to the external threads on the intra-implant part of the drug delivery assembly. The intra-implant part is threaded into the inlet of the device. Fig: B is a 3D rendered view of Fig A.

Figure 5:
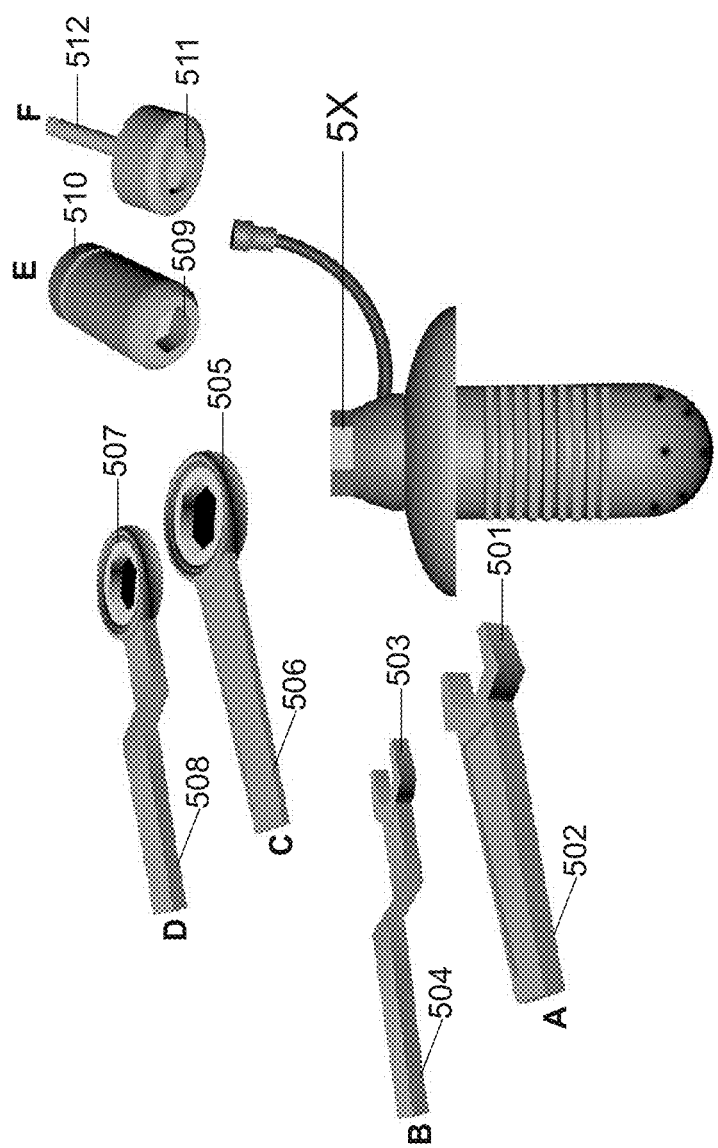
FIG. 5 shows the placement and removal tools (501, 503, 505, 507, 509, 511) for use with the device.

The drug delivery device is held and placed in the surgical site using specialized holding devices because of the limited anatomical space available for use and the need for sterilized instruments. The instruments are configured as hand held or as motor driven rotary instruments. The hand held instruments can be in the form of ratchets or spanners of varying sizes and length. The holding devices basically consist of a head and a handle. The head adapts to the external hex present on the drug delivery device or on the retention cap. The head can be of varying diameters. The handle can be of varying lengths and angulations. The handle can be hand held or be attached to a low-speed motor driven rotary handpiece. The embodiments are illustrated in FIG. 5. Referring to FIG. 5, 5X refers to the external hex on the device Fig: A Refers to the spanner for placement and removal. 501. Refers to the head which adapts to the external hex on the device. 502. Refers to the handle. Fig: B Refers to an angulated spanner. 503. Refers to the head which adapts to the external hex on the device. 504. Refers to the angulated handle. Fig: C refers to the hand-held ratchet. 505. Refers to the head which adapts to the external hex on the device. 506. Refers to the handle. Fig: D refers to an angulated hand-held ratchet. 507. Refers to the head which adapts to the external hex on the device. 508. Refers to the angulated handle. Fig: E refers to a hand-held rotating placement and removal tool. 509. Refers to the head which adapts to the external hex on the device. 510. Refers to the rotating finger rest. Fig: F refers to a motor driven rotary placement and removal tool. 511. Refers to the head which adapts to the external hex on the device. 512. Refers to the free end of the shank that can fit into the rotary instrument.

Figure 6:
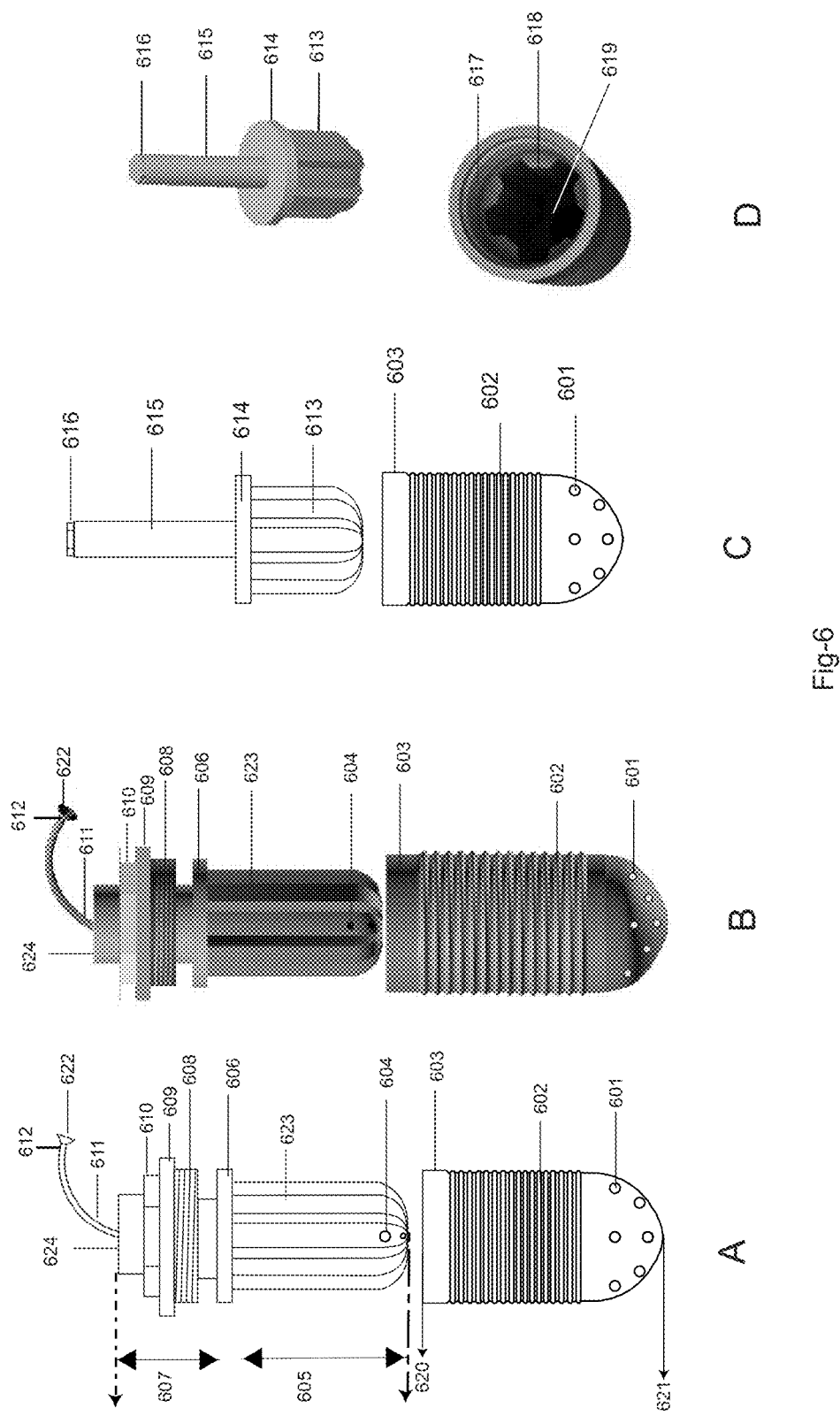
FIG. 6 shows the device in the form of a dental implant (619) with an internal spline (618) in the internal wall of body of the implant.

Another embodiment is illustrated in FIG. 6. In this embodiment, the device is in the form of a hollow dental implant made of titanium alloy or any other biocompatible material. The implant comprises external threads (602) on the body. The implant has micro holes (601) at the apical part of the implant body. The central lumen (619) of the implant is defined by the internal surface of the implant and communicates with the nasal respiratory mucosa or the maxillary sinus lining mucosa through the holes (601) at the apical part of the body of the implant. The implant has an internal involute spline (618) within the implant body. The implant has internal threads (617) at the cervical end. The disposable abutment made of a bio-compatible material has a body comprising an intra-oral part (607) and an intra-implant part (605) with a barrier ring (606) disposed on the external surface between the two parts. The external surface of the intra-implant part of the abutment has an external involute spline (623) and a micro-porous apical wall (604). The abutment further comprises a central lumen that communicates to the exterior through an external drug delivery tubing (611) that extends from the first end (624) of the abutment. The external involute spline (623) of the abutment fits into internal involute spline (618) of the dental implant. The plurality of holes (604) at the apical wall of the abutment is in alignment and in line with the plurality of holes (601) at the apical wall of the implant. A cap (609) comprising an external hex (610) with a central hole at the upper first part and external threads (608) at the lower second part is slid from the top of the abutment and threaded into the inner threads (617) at the cervical part of the implant. The inner aspect of the cap adapts closely and tightly to the outer surface of the abutment to form a tight junction without any micro-leakage. The cap (609) of the device can be of variable heights depending on the soft tissue requirements and is well adapted to the wall of the abutment on tightening. The drug is delivered into the central lumen of the abutment through the external drug delivery tubing (611) extending from the first end of the abutment. Fig: A refers to the isometric side view of the dental implant 601 refers to the holes in the apical wall of the implant. 602 refers to the external threads on the implant. 603 refers to the smooth cervical end. 604 refers to the holes in the apical wall of the abutment. 605 refers to the intra implant part. 623 refers to the external involute spline on the abutment. 606 refers to the barrier ring. 607 refers to the intra-oral part of the abutment. 608 refers to the external threads on the cap. 609 refers to the cap. 610 refers to the external hex on the cap. 624 refers to the first end of the abutment. 611 refers to the external drug delivery tubing. 612 refers to the distal free end of the external drug delivery tubing. 622 refers to the cap removably coupled to the open end of the external drug delivery tubing. 620 refers to the first open end of the device. 621 refers to the second end of the device. Fig: B refers to the 3 D rendered view of Fig A. Fig: C refers to the isometric side view of the dental implant and the placement tool. 601 refers to the holes in the apical wall of the implant. 602 refers to the external threads on the implant. 603 refers to the smooth cervical end. 613 refers to the external involute spline on the placement tool. 614 refers to the barrier ring on the placement tool. 615 refers to the shank of the placement tool. 616 refers to the external hex on the hand-held placement tool. Fig: D refers to the 3 D rendered view of Fig C. 613 refers to the external involute spline on the placement tool. 614 refers to the barrier ring on the placement tool. 615 refers to the shank of the placement tool. 616 refers to the external hex on the hand-held placement tool. 617 refers to the internal cervical threads at the first open end of the implant. 618 refers to the internal spline within the implant. 619 refers to the central lumen within the implant.

Figure 7:
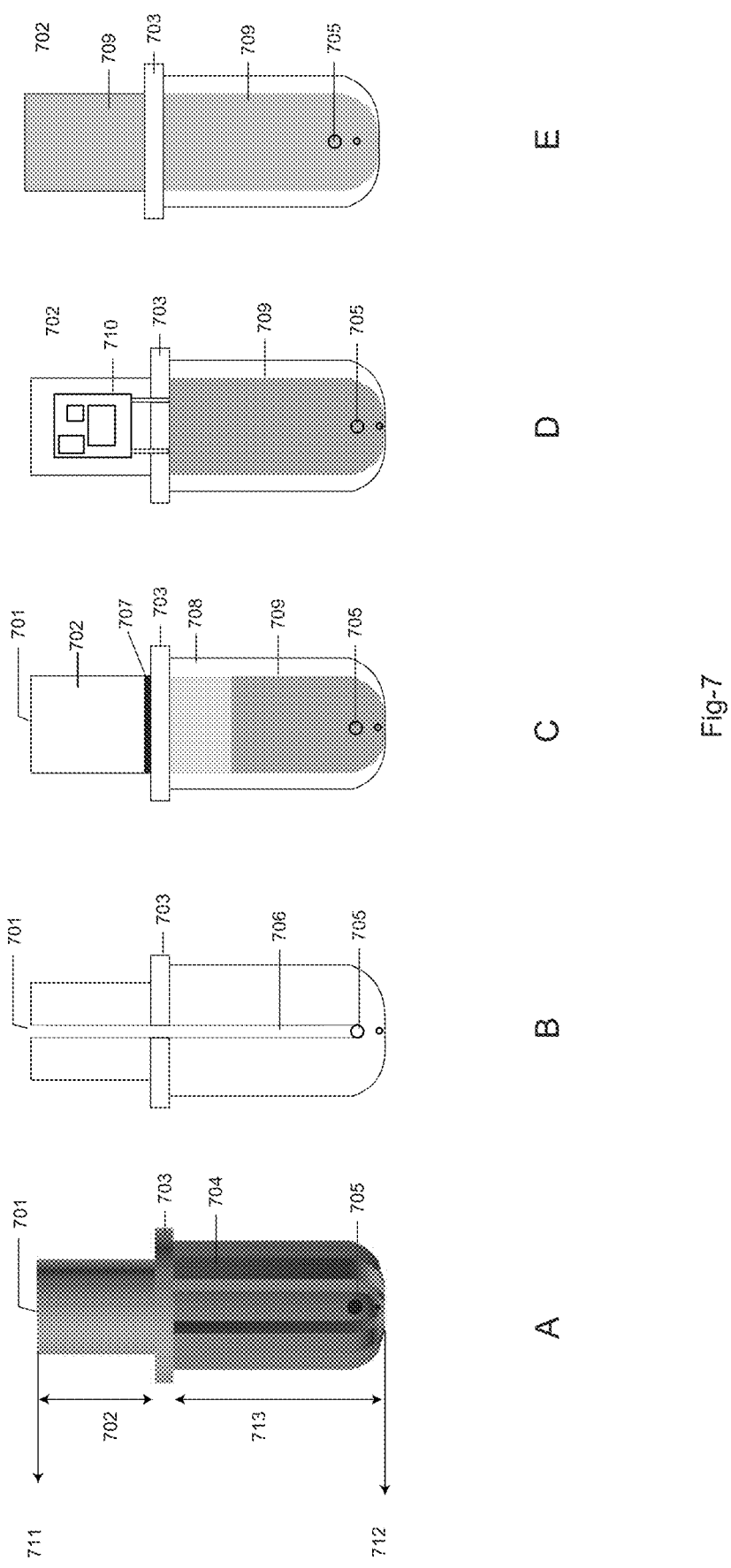
FIG. 7 shows an abutment in the form of a drug infusion source comprising a miniaturized internal drug infusion pump (710) and an internal drug reservoir (709) that is placed into the device in the form of a dental implant.

Alternative embodiments of the abutment, for use with the device in the form of a dental implant are illustrated in FIG. 7. Referring to FIG. 7, Fig A is a 3D rendered view of the abutment. 711 refers to the first end of the abutment. 712 refers to the second end of the abutment. 702 refers to the first part or the intra-oral part of the abutment. 713 refers to the second part or the intra-implant part of the abutment. 701 refers to the inlet in the first end of the abutment. A drug delivery tubing is removably secured to the inlet. 703 refers to the barrier ring. 704 refers to the external involute spline. 705 refers to the openings in the apical wall. Fig B is the longitudinal section of Fig A. 706 refers to the central lumen within the body of the implant. In another alternative embodiment, specially designed abutments in the form of drug reservoirs comprising in-built, miniature, osmotically or electronically controlled infusion pumps are used for drug delivery with the device. Fig C refers to the abutment comprising a drug reservoir in the second part, a space to hold an injected osmotic solvent in the first part and an osmotic compartment holding the osmotic agent disposed between the first and the second part. A semipermeable membrane separates the osmotic agent from the space in the first part. When the solvent is injected into the space in the first part, the solvent moves across the semipermeable membrane into the osmotic compartment and causes it to expand, thereby pushing the drug out from the reservoir at a predetermined rate through the apical holes. 701 refers to the inlet in the first end of the abutment through which the osmotic solvent is delivered. 702 refers to the intra-oral part of the abutment that holds the osmotic solvent. 703 refers to the barrier ring. 705 refers to the openings in the apical wall. 707 refers to the semipermeable membrane separating the osmotic agent from the space in the first part of the abutment. 708 refers to the osmotic compartment. 709 refers to the drug reservoir. Fig D refers to the abutment comprising a drug reservoir in the second part and an electronic drug infusion pump in the first part. 702 refers to the intra-oral part of the abutment that holds the electronic drug infusion pump. 703 refers to the barrier ring. 705 refers to the openings in the apical wall. 709 refers to the drug reservoir. 710 refers to the electronic drug infusion pump. The abutment can also be used as a drug reservoir for continuous drug delivery, by modifying the size of the plurality of holes at the apical part of the abutment into holes that equal the size of the drug molecule. This results in delivery of the drug molecules at a pre-determined rate. Fig E refers to the abutment used as an internal drug reservoir. 702 refers to the first part or the intra-oral part of the abutment. 703 refers to the barrier ring. 705 refers to the openings in the apical wall. 709 refers to the drug reservoir compartment extending from the first part to the second part of the abutment. The intra oral part of the abutment can be angulated above the level of the cervical ring (809). The inlet on the abutment can also be in the form of an opening with internal threads and located on the side of the intra-oral part.

Figure 8:
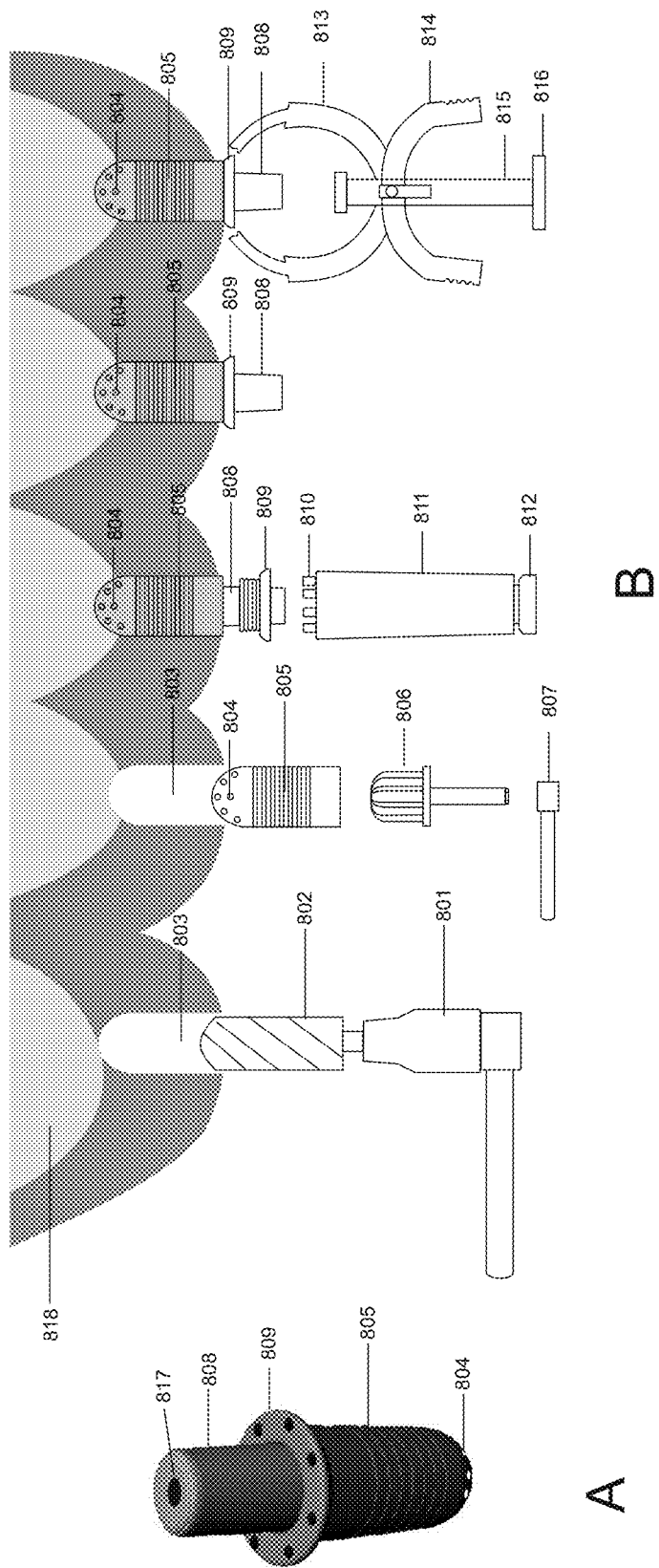
FIG. 8 shows the surgical placement of the device in the form of a dental implant (805) in the maxillary alveolar ridge (803), along with the placement and removal tools (806, 811, 815).

In the case of preparing the surgical site on the maxillary alveolar process, an osteotomy dental drill of appropriate length and diameter is used. The osteotomy is stopped short by 1 mm of the maxillary sinus lining mucosa or the nasal respiratory mucosa. The apical 1 mm of bone is gently broken with a bone compression tool or with an elevator by gentle tapping. Care is taken not to tear the respiratory mucosa in the nasal or the maxillary sinus region. Placement of the device in the form of a dental implant into the alveolar bone using the required instruments is illustrated in FIG. 8, 801. Refers to the ratchet for holding the bone compression tool. 802 refers to the bone compression tool being used for enlarging the soft osteotomy site and for breaking the apical wall to access the respiratory mucosa. 803 refers to the osteotomy site in the maxillary region underlying the respiratory mucosa. 804 refers to the holes in the apical wall of the implant. 805 refers to the body of the implant being placed into the osteotomy site. 806 refers to the placement tool used for placing the device into the osteotomy. 807 refers to the ratchet for holding the placement tool. 808 shows the abutment placed into the device. 809 shows the cervical retention cap comprising a central hole being placed across the intra oral part of the abutment. The cap further comprises a plurality of holes disposed on the superior surface of the upper part. 810 refers to the projections at the tip of the placement tool that removably secure to the holes on the superior surface of the upper part of the cap. 811 refers to the body of the placement tool. 812 refers to the rotating finger rest on the placement tool. 813 refers to the claw of the removal tool. 814 refers to the handle of the removal tool. 815 Refers to the vertically moveable shank of the device. 816 refers to the rotating finger rest on the removal tool. 817 refers to the inlet in the upper end of the abutment. 818 refers to the maxillary sinus or the nasal cavity comprising respiratory lining mucosa.

Another embodiment illustrated in FIG. 9. is an implantable drug delivery device that comprises a mini plate with a central drug reservoir dial, wherein the reservoir has a porous base, a body with parallel walls, external or internal threads at the top part of the dial wall and a cap with complimentary internal or external threads made of a resilient, biocompatible material that self-seals whenever penetrated by a needle. The porous base of the drug reservoir dial comprises macro holes, micro holes or nano holes and is placed beneath or above the respiratory mucosa. The drug is delivered into the drug reservoir dial using a needle that is connected to a syringe or an external drug infusion pump. The needle penetrates the cap and deposits the drug into the drug reservoir dial. Alternatively, a reservoir containing a drug with a rate limiting membrane at the base can also be placed into the dial. The drug reaches the respiratory mucosa through the holes in the base of the drug reservoir dial. The mini plate is secured to the bone by screws. Referring to FIG. 9, Fig A shows the top view of a mini plate that comprises a central drug reservoir dial with a microporous or nanoporous apical wall at the second end and straight limbs. 901 refers to the straight limb with screw holes. 902 refers to the inlet at the first open end of the central drug reservoir dial with internal or external threads. A cap (906) with complimentary threads is secured to the inlet of the drug reservoir dial. 903 refers to the micro-porous or nanoporous apical wall at the second end of the drug reservoir dial. The drug is deposited into the dial. 908 refers to the retention screw. Fig B shows a top view of the mini plate that comprises a central drug reservoir dial with a microporous or nanoporous apical wall at the second end and a left L shaped limb. 901 refers to the straight limb with screw holes. 902 refers to the inlet at the first open end of the central drug reservoir dial with internal or external threads. A cap with complimentary threads is secured to the inlet at the first open end of the drug reservoir dial 903 refers to the micro-porous or nanoporous apical wall at the second end of the drug reservoir dial. The drug is deposited into the dial. 904 refers to the left L shaped limb with screw holes. Fig C shows the top view of a mini plate that comprises a central drug reservoir dial with a microporous or nanoporous apical wall at the second end and a right L shaped limb. 901 refers to the straight limb with screw holes. 902 refers to the inlet at the first open end of the central drug reservoir dial with internal or external threads. A cap with complimentary threads is secured to the inlet at the first open end of the drug reservoir dial 903 refers to the micro-porous or nanoporous apical wall at the second end of the drug reservoir dial. The drug is deposited into the dial. 904 refers to the right L shaped limb with screw holes. Fig D shows the cap made of a resilient, biocompatible material that self-seals whenever penetrated by a needle. 905 refers to the holes used for holding the cap while threading it onto the reservoir dial. 906 refers to the self-sealing part of the cap into which needles can be inserted. 907 refers to the threads on the cap. The threads can be external or internal.

Figure 10:
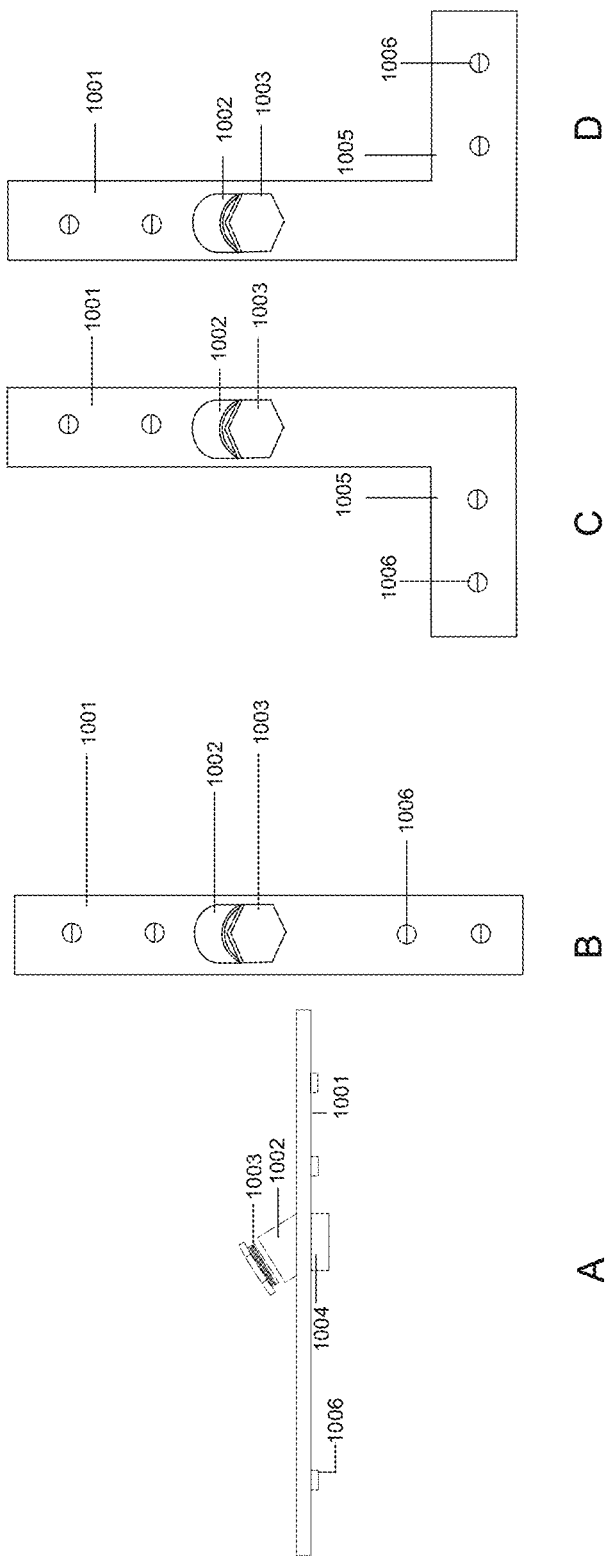
FIG. 10 shows a mini plate (A, B, C, D) with a reservoir dial comprising an angulated upper body (1002) for ease of access.

An alternative embodiment comprises a mini plate with a central reservoir dial wherein the reservoir has a porous base, an angulated body and a cap made of a resilient, biocompatible material that self-seals whenever penetrated by a needle. The upper end of the cap has an external hex and the lower part of the cap has internal or external threads. The angulation helps in ease of placing the needle tip into the reservoir for drug delivery from the oral cavity, when the mini plate is located on concave surfaces like the anterior wall of the maxillary sinus. The alternative embodiment is herein illustrated in FIG. 10. Referring to FIG. 10, Fig A shows the side view of a mini plate with a central drug reservoir dial, comprising a hollow body with an angulated first part and a perpendicular second part, a straight limb and an L shaped limb between the two parts of the dial. 1001 refers to the straight limb with screw holes. 1002 refers to angulated part of the central drug reservoir dial comprising an inlet with internal or external threads at the first open end. 1003 refers to the cap with threads 1004 refers to the perpendicular second part of the reservoir dial comprising a micro-porous or nanoporous apical wall at the second end that is placed below the respiratory mucosa. 1006 refers to the retention screw. Fig B shows the top view of a mini plate with a central drug reservoir dial, comprising a hollow body with an angulated first part and a perpendicular second part with straight limbs between the two parts of the dial 1001 refers to the straight limb with screw holes. 1002 refers to angulated part of the central drug reservoir dial comprising an inlet with internal or external threads at the first open end. 1003 refers to the cap with threads. 1006 refers to the retention screw. Fig C and D show the top view of a mini plate with a central angulated drug reservoir dial comprising a straight limb and an L shaped limb. 1001 refers to the straight limb with screw holes. 1002 refers to angulated part of the central drug reservoir dial comprising an inlet with internal or external threads at the first open end. 1003 refers to the cap with threads 1005 refers to the L shaped limb. It can point either to the right or to the left. 1006 refers to the retention screw.

II. Method for Drug Delivery:

A. Surgical Preparation of the Implantation Site

A full thickness buccal or palatal mucoperiosteal flap is elevated. A bone window is marked on the bone overlying the respiratory mucosa using a bone trephine drill of appropriate length and diameter. The bone window can be surgically prepared at a number of anatomical sites which also include the hard palate forming the floor of the maxillary sinus or the nasal cavity, anterior wall of the maxillary sinus or the zygomatic process of the maxilla. The bone window can be gently pried out with the rotating trephine drill without damaging the underlying respiratory mucosa. Alternatively, the circumscribed bone can be removed gently without damaging the underlying mucosa using a piezo instrument. The respiratory mucosa is gently released and elevated from the surrounding bone margins without tearing the respiratory mucosa by using a soft tissue elevator of appropriate diameter.

In the case of preparing the surgical site on the maxillary alveolar process, an osteotomy dental drill (802) of appropriate length and diameter is used. The osteotomy (803) is stopped short by 1 mm of the maxillary sinus lining mucosa or the nasal respiratory mucosa. The apical 1 mm of bone is gently broken with a bone compression tool or with an elevator by gentle tapping. Care is taken not to tear the respiratory mucosa in the nasal or the maxillary sinus region.

B. Surgical Placement of the Implant

A ratchet or implant placement tool (FIG. 5: A. B, C, D, E, F) which fits onto the external hex (1110; 1210) on the implant is used to hold and place the implant. The implant of the correct diameter and length is gently threaded into the prepared osteotomy site using a hand-held ratchet or a rotary placement tool. Alternatively, the implant can be gently press fit into the osteotomy hole. The barrier ring (1107; 1207) prevents the accidental displacement of the implant into the maxillary sinus or the nasal cavity. The respiratory lining mucosa (1101) is further elevated by the smooth apical end of the implant. The porous apical part (1102) of the hollow implant is thus in contact with the connective tissue base of the respiratory lining mucosa. The drug delivery assembly or the delivery tubing (1108) is attached to the implant at the inlet. The elevated soft tissue flap is placed back in position and sutures are placed. The surgical site is allowed to heal. The second open end of the drug delivery tubing can be placed in the buccal sulcus overlying the oral mucosa, in the buccal gingival sulcus or in the palatal gingival sulcus. The second open end of the tubing 1109) can be closed with a temporary cap (1111). After adequate healing of the surgical site, whenever drug delivery is required the can is removed and the second open end of the tubing can be attached to a drug infusion source comprising an external drug infusion pump (1305) and an external drug reservoir for controlled drug delivery.

C. Location of the Apical Porous Tip of the Device with Respect to the Respiratory Mucosa The porous apical wall of the device can be surgically placed beneath the intact respiratory mucosa at a number of anatomical sites which also include the maxillary sinus, hard palate forming the floor of the nasal cavity or maxillary sinus, the zygomatic process of the maxilla or the nasopalatine foramen. The drug can be delivered in a continuous and controlled manner into the connective tissue side of the respiratory mucosa, through the plurality of holes in the apical wall of the hollow device, by connecting the drug delivery tubing of the device to an external drug reservoir that is attached to a drug infusion pump. The drug distributes into the brain by bypassing the blood brain barrier from the delivery site without increasing the concentration of the drug in the peripheral circulation. The drug delivery route into the brain can either be through the neural, lymphatic or the vascular route or a combination of all the routes. This is useful for drugs which need to be given in precise concentrations and in low volumes. Drugs can thus be delivered into the brain by bypassing the blood brain barrier.

Referring to FIG. 11: Fig: A refers to the isometric view of the maxillofacial implantable drug delivery device placed beneath the nasal respiratory mucosa or the maxillary sinus lining mucosa. 1101 refers to the respiratory mucosal lining. 1102 refers to the smooth porous apical wall of the device. 1103 refers to the drug delivered under the respiratory mucosa. 1104 refers to the surrounding alveolar bone. 1105 refers to the overlying oral mucosa. 1106 refers to the threads on the outer surface of the device. 1107 refers to the barrier ring. 1108 refers to the drug delivery tubing. 1109 refers to the second open end of the drug delivery tubing. 1110 refers to the external hex. 1111 refers to the can. Fig B is a 3D rendered view of Fig A.

The porous apical tip of the device can also be placed into the maxillary sinus and above the level of the epithelial lining of the respiratory mucosa by perforating the respiratory mucosa from underneath or the connective tissue side. The drug can be delivered from an external drug reservoir into the maxillary sinus and onto the epithelial surface of the mucosal lining, in a continuous and controlled manner through the plurality of holes at the apical wall of the device by using an external drug infusion pump. The drug can then be easily inhaled during inspiration since the air in the normal maxillary sinus empties during routine inspiration and fills with air during expiration. The inhaled drug can be further deposited on the nasal respiratory and olfactory mucosa for absorption. Moreover because of the mucociliary action, the drug can also be transported from the maxillary sinus onto the nasal respiratory mucosa through the ostial opening at the middle meatus. This drug can be further be inhaled to reach the olfactory mucosa also. Because of the extra time taken for muco ciliary clearance from the maxillary sinus to the nasal respiratory mucosa, the retention time of the drug on the mucosal surface is increased, resulting in absorption of higher quantity of the drug. This route is useful for drug formulations that are inhalable and can be given in larger volumes without causing systemic or local complications.

Referring to FIG. 12: Fig: A refers to the isometric view of the maxillofacial implantable drug delivery device placed into the maxillary sinus with the tip above the level of the epithelial lining of the lining respiratory mucosa. 1201 refers to the respiratory mucosal lining. 1202 refers to the smooth microporous apical wall of the device. 1203 refers to the drug delivered above the respiratory mucosa. 1204 refers to the surrounding alveolar bone. 1205 refers to the overlying oral mucosa. 1206 refers to the threads on the outer surface of the device. 1207 refers to the barrier ring. 1208 refers to the drug delivery tubing. 1209 refers to the second open end of the drug delivery tubing. 1210 refers to the external hex. 1211 refers to the can. Fig B is a 3D rendered view of Fig A.

D. Controlled and Continuous Drug Delivery.

The second open end of the drug delivery tubing which is located over the oral mucosa in the buccal sulcus, at the buccal gingival sulcus or the palatal gingival sulcus is connected to a drug infusion source comprising an external reservoir attached to an external drug infusion pump. The external electronically controlled infusion pump provides a continuous and controlled rate of delivery of drugs at the range of milliliters, microliters or nanoliters into the implant.

Figure 13:
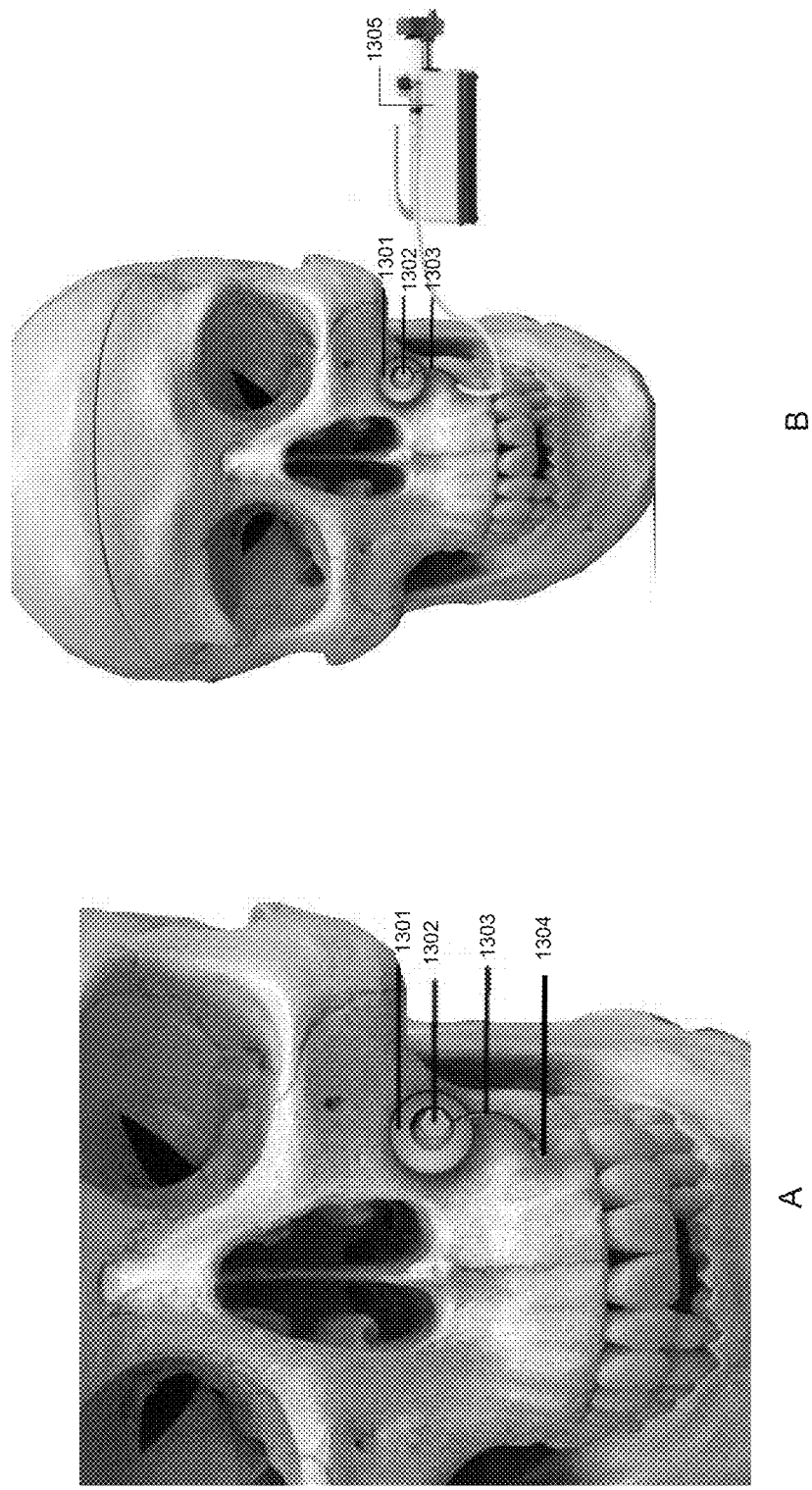
FIG. 13 shows the device (1302) placed on the anterior wall of the maxillary sinus with the drug delivery tubing (1303) extending into the buccal sulcus. The drug delivery tubing is connected to a drug infusion source comprising an external drug infusion pump (1305) and an external drug reservoir for continuous and controlled drug delivery.

This is essential to provide drug delivery without traumatizing the respiratory mucosa, to prevent backflow of drug from the device due to high rate of drug inflow and to prevent leakage or overflow of the drug across the mucosal delivery site due to high rate and large volume of drug delivery at the implant-mucosal interface. The preferred method is illustrated in FIG. 13. Fig A shows the device placed at the anterior wall of the maxillary sinus. 1301 refers to the barrier ring. 1302 refers to the external hex. 1303 refers to the drug delivery tubing. 1304 refers to the cap Fig B shows the device connected to an external drug reservoir attached to an external drug infusion pump. 1305 refers to the external drug infusion pump comprising an external drug reservoir that is attached to the second oven end of the drug delivery tubing of the device.

Alternatively, as in FIG. 7: C and D, an abutment comprising an internal drug reservoir (709) at the intra-implant part (713) which is controlled by a miniature drug infusion pump (710) located in the intra-oral part (702), can be used with the device in the form of a dental implant (805) for controlled and continuous drug delivery. This system can be used when the device is placed into the alveolar ridge (803), small quantity of drug has to be delivered over a period of time, and access is available to change the abutment after the drug is delivered. Alternatively, as in FIG. 7: E, the abutment can be used as a drug reservoir 709) for continuous drug delivery, by modifying the plurality of holes (705) at the apical part of the abutment into holes that equal the size of the drug molecule. This results in delivery of the drug molecules at a pre-determined rate.

Optional Procedures for Different Clinical Situations

In case of emergency, the drug can be directly delivered beneath the respiratory mucosa on the connective tissue side using the drug delivery assembly which is connected to an external drug reservoir attached to an external drug infusion pump.

A biocompatible cement can be applied to the undersurface of the barrier ring of the implant to fix the barrier ring to the underlying bone. This retains the implant in position and prevents movement during immediate drug delivery.

The barrier ring of the device can also be configured with screw holes at the periphery or with retentive limbs containing screw holes. Mini screws can be placed in the holes to secure the device to the bone.

Figure 14:
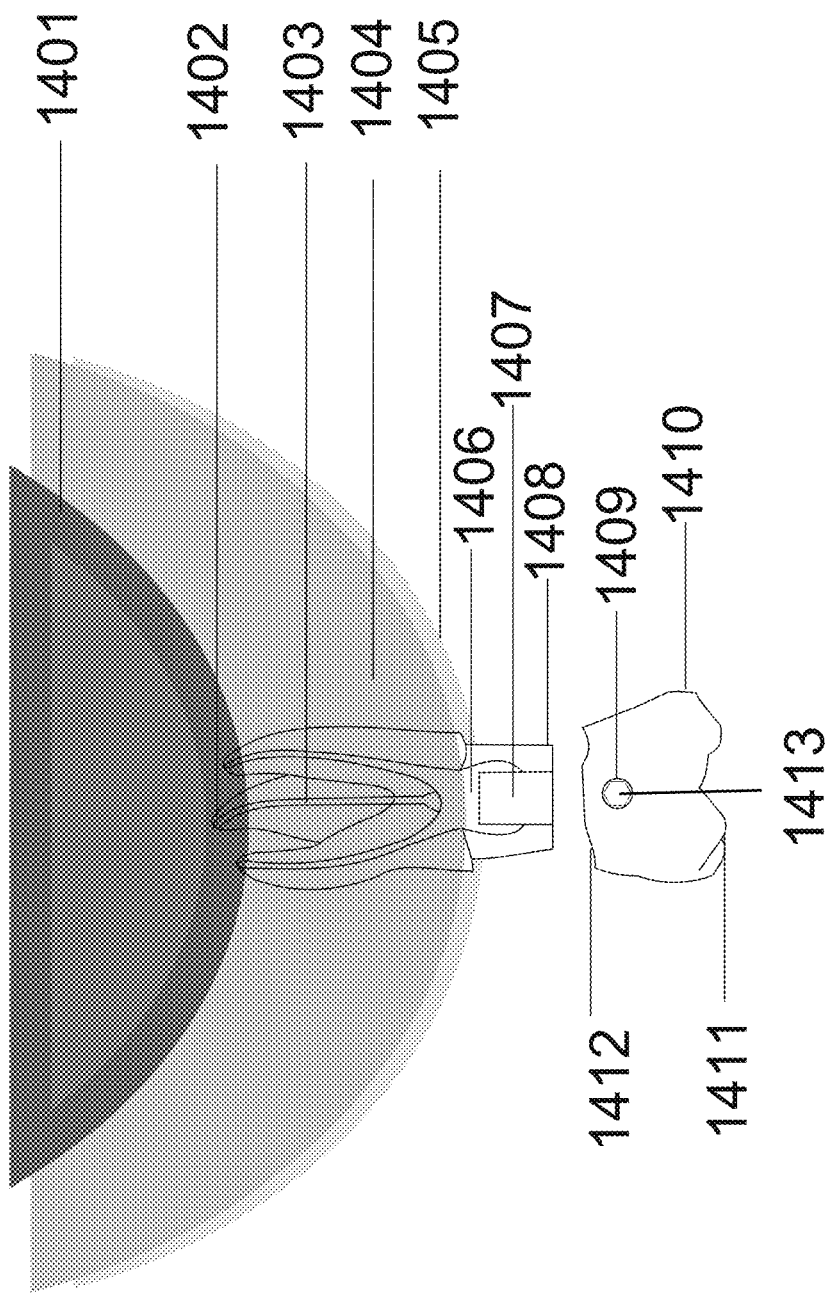
FIG. 14 shows the device in the form of a prosthetic crown (1410) that is secured to a root canal treated tooth (1408) whose apex (1402) is in contact with the respiratory mucosa (1401).

In another alternative embodiment as illustrated in FIG. 14, a device in the form of a prosthetic crown (1410) secured to a root canal treated tooth (1408) whose apex (1402) is in contact with the respiratory mucosa (1401) is used as a drug delivery device. After biomechanical preparation of the pulp cavity (1406;1403) of the tooth till the apex, the coronal part of the tooth (1408) is prepared for the crown. An additional vertical slot (1407) is prepared on the tooth extending from the occlusal surface to the middle part of buccal or palatal wall. A crown (1410) is made using a biocompatible material. A cylindrical tube open at both the ends is included as a part in the crown at the middle third of the palatal or buccal wall, further wherein the intra oral end of the tube (1409) that opens into the oral cavity at the buccal or palatal side has internal threads and the intra pulpal end of the tube that opens into the pulp chamber is smooth with a straight or an apically curved end. The part of the crown with the cylindrical tube is slid into the vertical slot (1407) in the coronal part of the tooth during the cementation of the crown. A drug delivery tubing is threaded into the open end (1409) of the inlet tube on the buccal or palatal side for drug delivery. The opening is closed with a disposable cap (1413) when not in use. FIG. 14 shows an upper molar with its root tips in close proximity to the overlying maxillary sinus lining mucosa. 1401 refers to the maxillary sinus lining. 1402 refers to the opening at the root apex. 1403 refers to the enlarged and debrided pulp canal. 1404 refers to the alveolar bone. 1405 refers to the gingiva. 1406 refers to the pulp chamber. 1407 refers to the vertical slot on the buccal wall. 1408 refers to the coronal part of the tooth prepared for receiving the prosthetic crown. 1409 refers to the drug delivery inlet on the prosthetic crown. 1410 refers to the body of the prosthetic crown. 1411 refers to the first end of the crown. 1412 refers to the second end of the crown. 1413 refers to the disposable cap.

In cases where the device is in the form of a dental implant (FIG. 6: A B C D; FIG. 8: A, B) that is placed into the alveolar ridge (803), a dental crown with a buccal or palatal inlet is used with an abutment that also has a corresponding inlet opening on the side of the intra-oral part. Drug is delivered into the implant through the inlet in the abutment which in turn is accessed through the inlet in the buccal or palatal wall of the crown. The inlet opening in the crown is closed with a screw when not in use for drug delivery.

In cases where mini plates (FIG. 9: A, B, C; FIG. 10: A, B, C, D) with drug reservoir dials (902,1002) are used, a full thickness mucosal flap is elevated. Appropriate diameter of bone is removed with a bur or a piezo instrument, without damaging the overlying respiratory epithelium. The dial is placed into the osteotomy with its porous base (903,1004) in contact with the respiratory mucosa. The mini plate is fixed to the bone by mini screws (908,1006). The top of the dial is closed with a threaded cap (906,1003) which is biocompatible and self-seals when penetrated by a needle. The flap is replaced over the reservoir and allowed to heal. Drug can be injected into the reservoir dial space using a needle from the overlying anaesthetized mucosa whenever needed.

E. Applications of the Delivery Device

The brain drug delivery implant can be used for a single dose of drug delivery and then removed or can be retained at the anatomical site for a longer period of time if multiple doses of the drug are required. A single drug or a combination of drugs can be delivered. Stem cells and small interference RNAs can also be delivered into the brain using this device and the methods.

Hence this device and the methods can be used to deliver the drugs into the brain bypassing the blood brain barrier in patients with Alzheimer, Parkinson, Drug addiction, Cancer, White matter disease, Pain management, Brain infections, Psychiatric conditions and a myriad of other relevant medical conditions.

The brain drug delivery device and the methods of drug delivery thereof will be further understood by reference to the following non-limiting examples.

EXAMPLE 1

Controlled and Continuous Delivery of Drugs Beneath the Respiratory Mucosa

Figure 15:
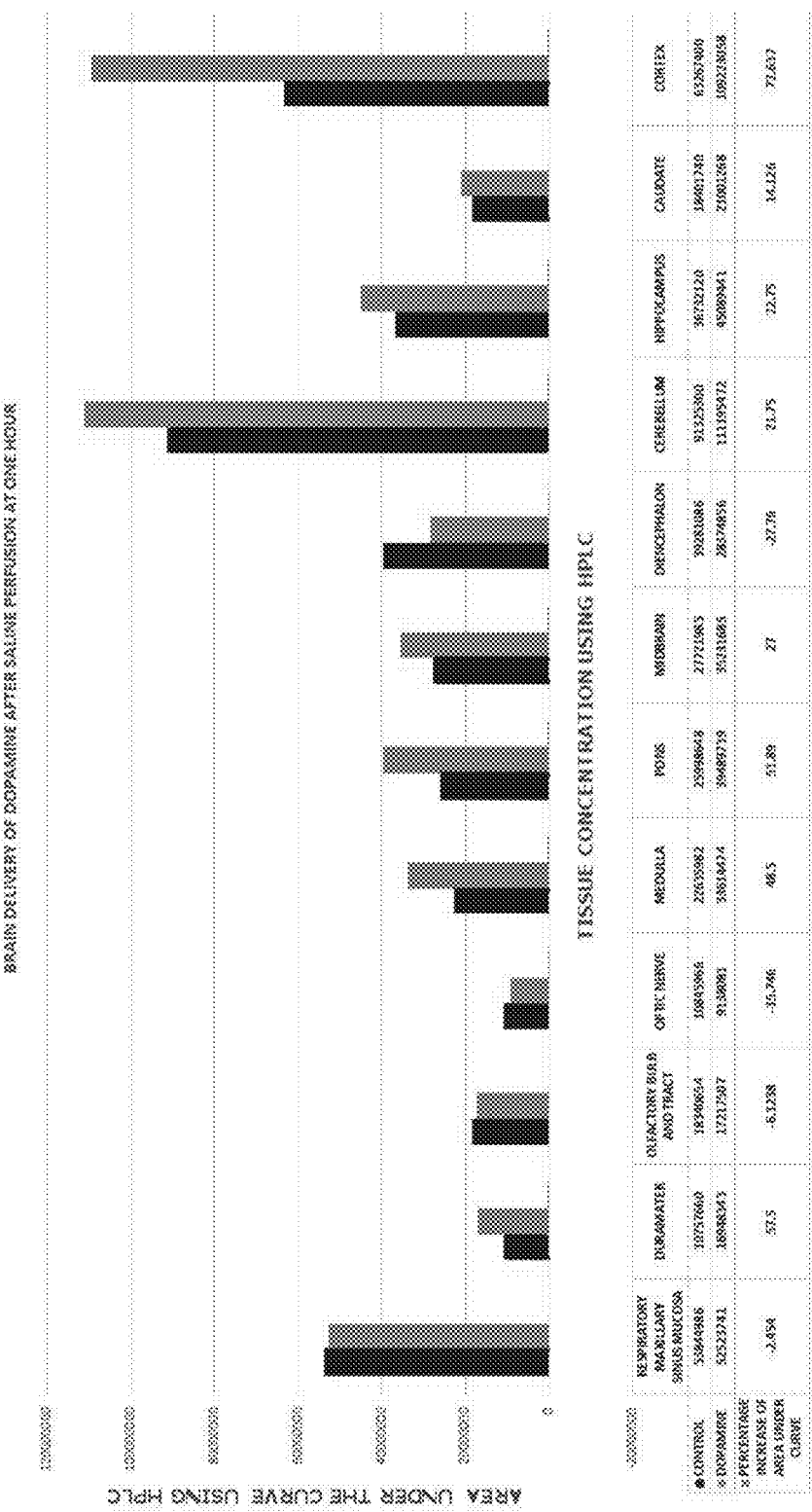
FIG. 15 shows the brain values of dopamine in a rabbit obtained using High performance Liquid Chromatography, after in vivo drug delivery of dopamine from beneath the respiratory mucosa.
Figure 16:
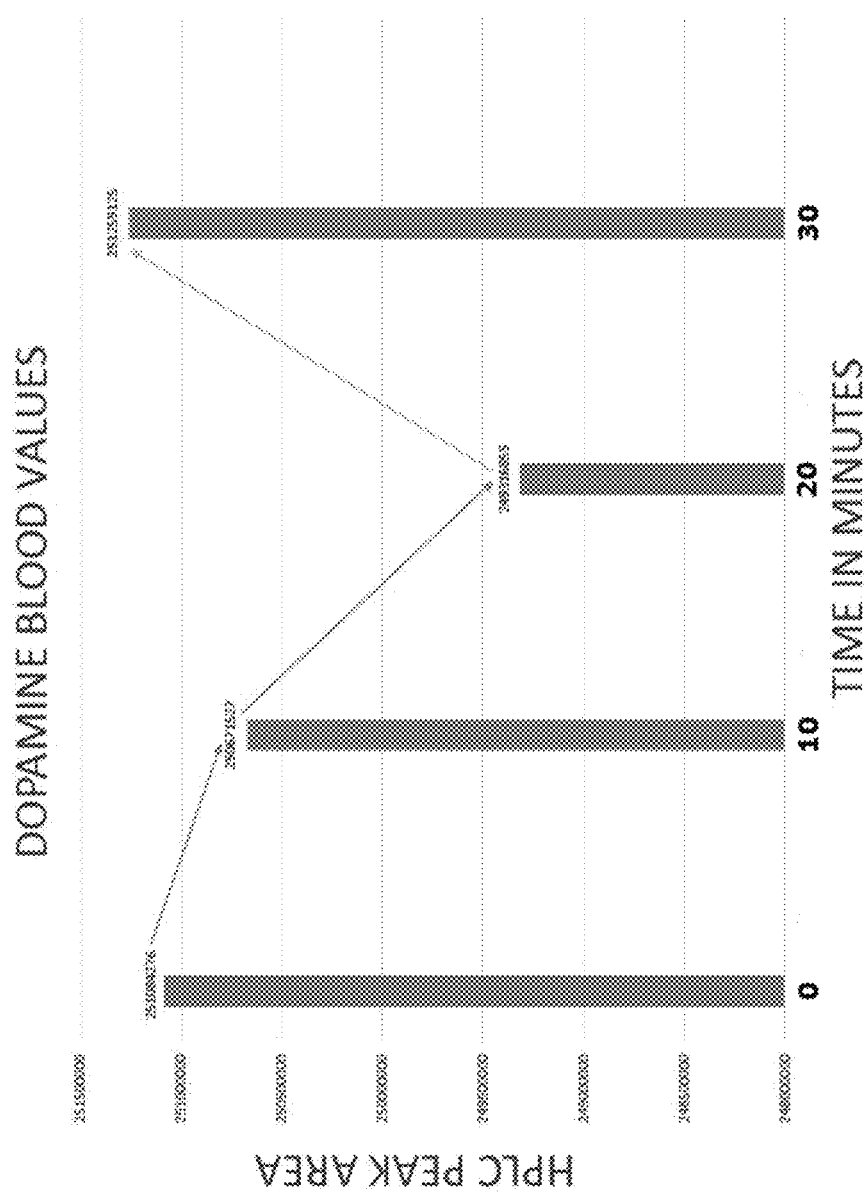
FIG. 16 shows the blood values of dopamine in a rabbit obtained using High performance Liquid Chromatography, after in vivo drug delivery of dopamine from beneath the respiratory mucosa.
Figure 17:
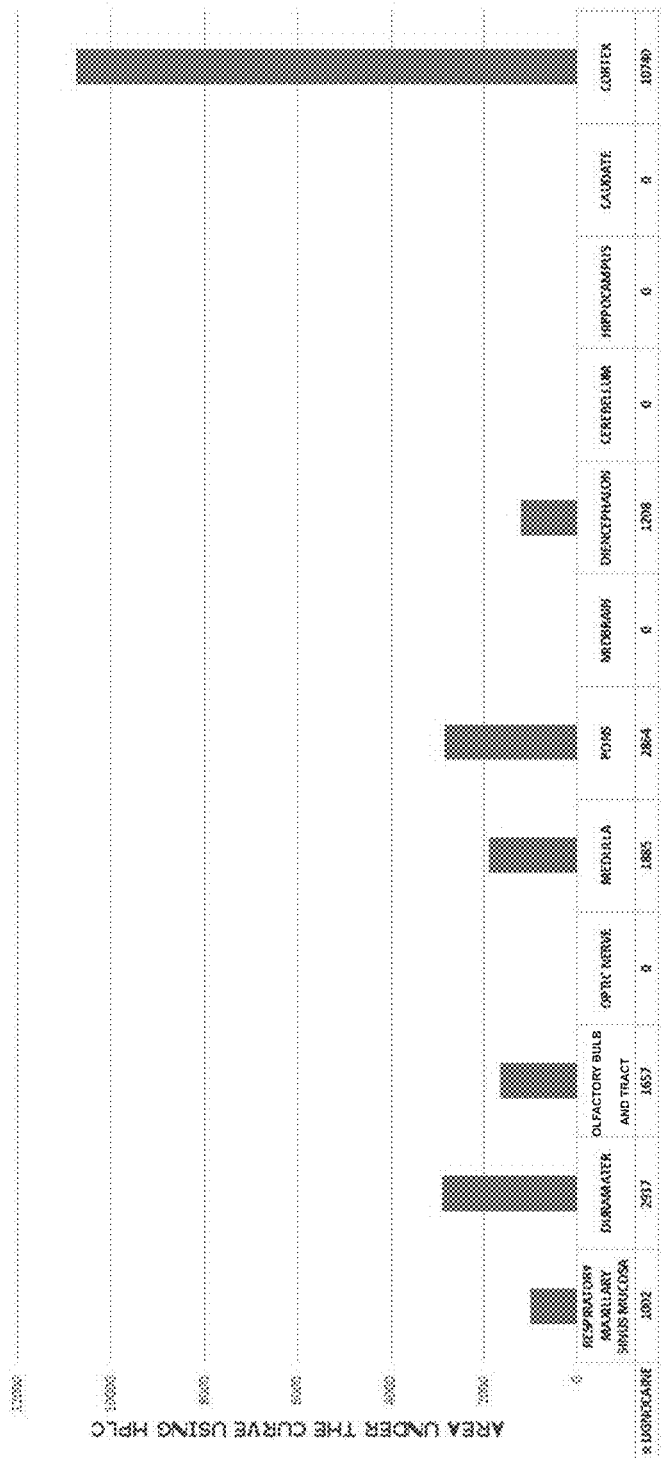
FIG. 17 shows the brain values of lignocaine in a rabbit obtained using High performance Liquid Chromatography, after in vivo drug delivery of lignocaine into the maxillary sinus and on the epithelial surface of maxillary sinus mucosa by perforating the lining mucosa from the connective tissue side.

The device was surgically placed in a rabbit in the maxillary sinus region by removing the bone overlying the respiratory mucosa. The tip of the device was placed beneath the maxillary sinus lining mucosa in contact with the connective tissue side of the mucosa. Dopamine was infused in a controlled and continuous manner under the maxillary sinus mucosa of the rabbit for twenty minutes at the rate of 1 milliliter per hour by using an external drug infusion pump connected to the implanted device. Whole body perfusion was done using a peristaltic pump with warm physiological saline for 20 minutes at a controlled rate. The perfused brain was then resected at the end one hour from the start of the procedure. Brain samples from different parts of the brain was analyzed using High Performance Liquid Chromatography. There was an increased concentration of dopamine in all parts of the brain except diencephalon when compared with the normal. Thus, the drug had bypassed the blood brain barrier. FIG. 15 refers to the comparative brain values of dopamine using High Performance Liquid Chromatography, between the control and the rabbit in which dopamine was delivered in vivo in a continuous and controlled manner under the maxillary sinus mucosa using the drug delivery system. During the procedure, a blood sample was collected before drug delivery. Three blood samples were then collected at intervals of 10, 20 and 30 minutes respectively following start of drug delivery. The samples were analyzed using High Performance Liquid Chromatography. The blood values dipped during drug delivery at the 10- and 20-minute interval. The drug delivery was stopped at the twentieth minute. Subsequently the blood value peaked again at the 30-minute interval. FIG. 16 refers to blood values of dopamine in the rabbit after in vivo delivery of dopamine under the maxillary sinus mucosa using the device. This shows that dopamine delivered using the device had reached the brain by bypassing the blood brain barrier and may have effected a low dopamine peripheral response by a feedback mechanism in the brain during drug delivery. The peripheral value would have increased after the central negative feedback control had ceased once the drug delivery was stopped. Moreover, there was no increase of the drug in peripheral circulation during drug delivery.

EXAMPLE 2

Controlled and Continuous Delivery of Drugs Above the Respiratory Mucosa

Figure 18:
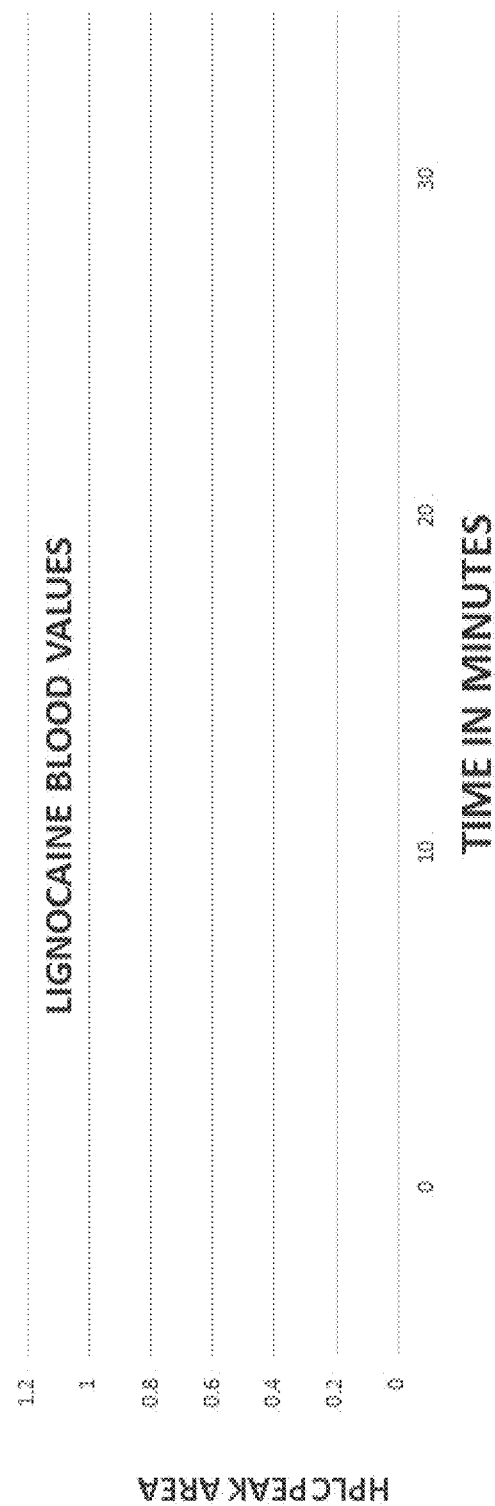
FIG. 18 shows the blood values of lignocaine in a rabbit obtained using High performance Liquid Chromatography, after in vivo drug delivery of lignocaine into the maxillary sinus and on the epithelia surface of maxillary sinus mucosa by perforating the lining mucosa from the connective tissue side.

The device was placed into the maxillary sinus of a rabbit by perforating the maxillary sinus mucosa from the connective tissue side and placing the implant tip into the sinus cavity and above the epithelial layer. Lignocaine was infused in a controlled and continuous manner for twenty minutes at the rate of 1.5 milliliter per hour by using an external drug infusion pump connected to the implanted device. Whole body perfusion was done using a peristaltic pump with warm physiological saline for 20 minutes at a controlled rate. The perfused brain was then resected at the end one hour from the start of the procedure. Brain samples from different parts of the brain was analyzed using High Performance Liquid Chromatography. There was an increased concentration of Lignocaine in some parts of the brain as shown in the FIG. 17. Thus the drug had bypassed the blood brain barrier. But the tissue distribution was lesser and the tissue concentration was less when compared to a similar volume of the drug delivered beneath the respiratory mucosa. During the procedure, a blood sample was collected before drug delivery. Three blood samples were then collected at intervals of 10, 20 and 30 minutes respectively following start of drug delivery. The samples were analyzed using High Performance Liquid Chromatography. There was no drug in the peripheral circulation. FIG. 18 refers to the blood values of Lignocaine in the rabbit after the in vivo delivery of Lignocaine into the maxillary sinus cavity and onto the epithelial surface of the maxillary sinus mucosa using the device The above-mentioned methods and device are only illustrative of the principle of the present invention. Modifications and variations of the methods and devices including but not limited to, variations in size, materials, shape, assembly, function, use and mode of operation will be obvious to those of ordinary skill in the art from the foregoing detailed description. Such modifications and variations made herein come within the scope of the appended claims.

We claim:

1. A drug delivery system for delivering drugs into a brain, by bypassing a blood brain barrier, comprising:
   a biocompatible implantable device comprising a hollow body disposed between a first closed end and a second end, wherein the hollow body comprises a first part comprising an inlet, a second part comprising an apical wall with a plurality of openings, said first part being positioned at the first closed end and said second part being positioned at the second end; and an internal wall defining a central lumen that forms a flow pathway from the inlet to the plurality of openings in the apical wall;
   a biocompatible tubing comprising a first open end, a second open end, at least one flow pathway between said first open end and said second open end, and a cap, wherein the first open end of the biocompatible tubing is configured to removably secure the biocompatible tubing to the inlet of the biocompatible implantable device and the cap is configured to removably couple to the second open end of the biocompatible tubing;
   a drug that is to be delivered to a connective tissue of a respiratory mucosa of a maxillary sinus or a nasal cavity for further transport into the brain;
   a drug infusion source comprising an external pump and an external drug reservoir containing said drug, wherein the drug infusion source is configured to removably couple to the second open end of the biocompatible tubing; and
   a holding device comprising a head portion positioned at an end of a handle, said holding device being configured to removably hold a portion of the first part of the biocompatible implantable device, wherein when the biocompatible implantable device is held by removably coupling the first end of the biocompatible implantable device to the head portion of said holding device and the second part of the hollow body of the biocompatible implantable device is inserted into a complimentary hole formed in a bone overlying the connective tissue of the respiratory mucosa of the maxillary sinus or the nasal cavity from an oral or maxillofacial region, the apical wall of the biocompatible implantable device comprising the plurality of openings is in contact with the connective tissue of said respiratory mucosa underlying the bone; further wherein when the drug infusion source is removably coupled to the second open end of the biocompatible tubing, said drug is delivered continuously at a controlled rate from the external drug reservoir to the central lumen of the biocompatible implantable device through the inlet and routed to the connective tissue of said respiratory mucosa through the plurality of openings in the apical wall.

2. The drug delivery system of claim 1 wherein the hollow body of the biocompatible implantable device is in the form of a hollow cylinder with the second end being a rounded second end.

3. The drug delivery system of claim 1 wherein the hollow body of the biocompatible implantable device is in the form of a tapering hollow tube with the second end being a rounded second end, further wherein the larger diameter is at the first end of the biocompatible implantable device and the smaller diameter is at the second end of the biocompatible implantable device.

4. The drug delivery system of claim 1 wherein the biocompatible implantable device further comprises a projection extending radially outwards from an external surface of the hollow body of the biocompatible implantable device and extending circumferentially around the external surface of the hollow body of the biocompatible implantable device to form a circular barrier ring between the inlet in the first part of the hollow body of the biocompatible implantable device and the plurality of openings in the second part of the hollow body of the biocompatible implantable device, wherein the circular barrier ring comprises a first surface configured to be in contact with an overlying soft tissue and a second surface configured to be in contact with an underlying bone.

5. The biocompatible implantable device according to claim 4, wherein the biocompatible implantable device further comprises threads on a portion of the external surface of a part of the hollow body that extends between the second surface of the circular barrier ring and the second end of the biocompatible implantable device.

6. The drug delivery system of claim 1 wherein the biocompatible tubing is in the form of a drug delivery assembly comprising:

the first open end configured in the form of a plurality of openings in an apical wall of an intra-implant part of the drug delivery assembly, said intra-implant part comprising a hollow tapering body disposed between a closed end and the plurality of openings in the apical wall of the intra-implant part, said hollow tapering body further comprising an internal wall defining a tapering central lumen that forms the at least one flow pathway from the closed end of the intra-implant part to the plurality of openings in the apical wall of the intra-implant part;

the second open end of the biocompatible tubing being disposed at an open end of an external tubing part of the drug delivery assembly, said external tubing part extending from a portion of the intra implant part and comprising a hollow tubular body, said hollow tubular body further comprising an internal wall defining a cylindrical central lumen that forms the at least one flow pathway from the open end of said external tubing part to the central lumen of the intra-implant part; and the cap configured to removably couple to the open end of the external tubing part, wherein when the intra-implant part is inserted into the inlet of the biocompatible implantable device, at least a complimentary portion of the hollow tapering body of the intra-implant part is configured to adapt into the central lumen of the biocompatible implantable device and, at least a portion of the mesial part of the external tubing part is configured to removably adapt into a vertical slot in the inlet of the biocompatible implantable device, further wherein the open end of the external tubing part is configured to removably couple to the drug infusion source.

7. The drug delivery system of claim 1 wherein the biocompatible implantable device is in the form of a multiunit biocompatible implantable device comprising:

the first closed end comprising a removable cap;
the removable cap comprising an external hex in a first part and internal threads in a second part, said external hex in the first part being configured to removably couple to the holding device and said internal threads being configured to removably couple to the inlet in the first part of the hollow body of the biocompatible implantable device, and the inlet being a tubular inlet comprising complimentary threads;

the second end being a rounded second end;

the hollow body being a hollow cylindrical body with the central lumen being a tapering central lumen, the tubular inlet being positioned at the end of the first part of the hollow cylindrical body, wherein the tapering central lumen forms the flow pathway from the tubular inlet to the plurality of openings in the apical wall, wherein a wall of the tubular inlet further comprises a vertical slot extending from a tip of the tubular inlet; wherein the biocompatible tubing is configured in the form of a drug delivery assembly having a configuration complimentary to the tapering central lumen of the hollow body of the biocompatible implantable device, further wherein when the drug delivery assembly is inserted into the tubular inlet of the biocompatible implantable device, the drug delivery assembly adapts into said tapering central lumen and into the vertical slot in the tubular inlet of the biocompatible implantable device: the drug delivery assembly being retained within the biocompatible implantable device by removably coupling the removable cap to the tubular inlet of the biocompatible implantable device;

a circular barrier ring disposed on an external surface of the hollow body of the biocompatible implantable device between the tubular inlet in the first part of the hollow body of the biocompatible implantable device and the plurality of openings in the apical wall in the second part of the hollow body of the biocompatible implantable device;

an external hex disposed on the external surface of the hollow body of the biocompatible implantable device between the tubular inlet and the circular barrier ring; said external hex on the external surface of the hollow body being configured to removably couple the biocompatible implantable device to the holding device; and threads disposed at a cervical third of the external surface of a part of the hollow body of the biocompatible implantable device that extends between the circular barrier ring and the second end of the biocompatible implantable device.

8. The drug delivery system of claim 7 wherein the multiunit biocompatible implantable device further comprises the tubular inlet with internal threads, and wherein the drug delivery assembly comprises an external tubing part at a closed end of an intra-implant part, the intra-implant part further comprising external threads at a cervical third of the intra-implant part; said external threads of the intra-implant part being configured to removably secure to the internal threads of the tubular inlet of the biocompatible implantable device, the drug delivery assembly further comprising an external hex disposed between the external tubing part and the external threads of the intra-implant part, wherein when the drug delivery assembly is threaded into the tubular inlet of the biocompatible implantable device, an external wall of the intra-implant part adapts to the internal wall defining the central lumen of the biocompatible implantable device except at an apical part of the biocompatible implantable device, said apical part of the biocompatible implantable device the comprising a space defined by the external wall of an apical part of the intra-implant part of the drug delivery assembly and the internal wall defining the central lumen at the apical part of the biocompatible implantable device, further wherein when the drug is delivered through the external tubing part into a central lumen of the intra-implant part of the drug delivery assembly, said drug is routed to the space at the apical part of the biocompatible implantable device through a plurality of openings at the external wall at the apical part of the intra-implant part of the drug delivery assembly for further transfer to the exterior of the biocompatible implantable device through the plurality of openings at the apical wall of the biocompatible implantable device.

9. The drug delivery system of claim 1 wherein the biocompatible implantable device is in the form of a multiunit biocompatible implantable device comprising:
the first closed end comprising a removable cap;
the removable cap comprising an external hex in a first part and internal threads in a second part, said external hex in the first part being configured to removably couple to the holding device and said internal threads being configured to removably couple to the inlet in the first part of the hollow body of the biocompatible implantable device, the inlet being a tubular inlet comprising complimentary threads;
the second end being an open end comprising a beveled and outwardly flaring internal wall that forms a smooth and rounded margin;
the hollow body disposed between said first closed end and said second open end comprising the central lumen that forms a flow pathway from the tubular inlet in the first part of the hollow body to the second open end; the hollow body being a hollow cylindrical body with the central lumen being a tapering central lumen, the tubular inlet being positioned at the end of the first part of the hollow cylindrical body, wherein a wall of the tubular inlet further comprises a vertical slot extending from a tip to a middle third of the wall of the tubular inlet; wherein the biocompatible tubing is configured in the form of a drug delivery assembly having a configuration complimentary to the tapering central lumen of the hollow body of the biocompatible implantable device, further wherein when the drug delivery assembly is inserted into the tubular inlet of the biocompatible implantable device, the drug delivery assembly adapts into said tapering central lumen and into the vertical slot in the tubular inlet of the biocompatible implantable device, an end of the drug delivery assembly being positioned within a margin of the second open end of the biocompatible implantable device, and the drug delivery assembly being retained within the biocompatible implantable device by removably coupling the removable cap to the tubular inlet of the biocompatible implantable device,
a circular barrier ring disposed on an external surface of the hollow body of the biocompatible implantable device between the tubular inlet in the first part of the hollow body of the biocompatible implantable device and the open second end in the second part of the hollow body of the biocompatible implantable device;
an external hex disposed on the external surface of the hollow body of the biocompatible implantable device between the tubular inlet and the circular barrier ring; said external hex on the external surface of the hollow body being configured to removably couple the biocompatible implantable device to the holding device; and threads disposed at a cervical third of the external surface of the hollow body of the biocompatible implantable device that extends between the circular barrier ring and the second end of the biocompatible implantable device.

10. The drug delivery system of claim 1 wherein the biocompatible implantable device is in the form of a dental implant, comprising:
the hollow body of the biocompatible implantable device in the form of a hollow cylinder with the second end being a rounded end, wherein said inlet at an end of the first part of the hollow body comprising threads and being configured to removably couple to a removable cap with complimentary threads and wherein said internal wall comprising an internal involute spline and being configured to removably couple to the biocompatible tubing;
the biocompatible tubing in the form of a hollow abutment; wherein the hollow abutment comprises a hollow body comprising a first smooth intra-oral part and a second intra-implant part, said second intra-implant part further comprising an external involute spline configured to removably couple to the internal involute spline on the internal wall of the biocompatible implantable device; said hollow abutment further comprising a circular barrier ring disposed on an external surface of the body of the hollow abutment between said intra-oral part and the intra-implant part, further wherein the body of the hollow abutment comprises an inlet at an end of the intra-oral part of the hollow abutment in the form of an external drug delivery tubing removably coupled to the cap, a plurality of openings in the apical wall of the hollow abutment, and an internal wall defining a central lumen that forms at least one flow pathway from the inlet of the intra-oral part to the plurality of openings at in an apical wall of the hollow abutment; and
the first closed end of the hollow body comprising said removable cap, said removable cap comprising an external hex with a central hole in a first part and complimentary threads on a second part, wherein the external hex is configured to removably couple the biocompatible implantable device to the holding device, the second part of the cap comprising said complimentary threads is configured to removably secure to the threads of the inlet of the biocompatible implantable device, and the central hole of the removable cap is configured to removably adapt to an external surface of the intra-oral part of the body of said hollow abutment, whereby said hollow abutment is retained within the biocompatible implantable device by the removable cap.

11. The drug delivery system of claim 1 wherein the drug that is to be delivered to the connective tissue of the respiratory mucosa of the maxillary sinus or the nasal cavity for further transport into the brain; comprises:
drug molecules that are sized to aid drug delivery into the brain; and
have affinity to specific receptors in the brain, whereby the drug is configured to localize at targeted sites.

12. The drug delivery system of claim 1 wherein the holding device is configured in the form of a set of instruments in a surgical kit comprising a plurality of holding devices for placing and removing the biocompatible implantable device comprising:
a hand-held ratchet comprising a head at an end of a straight handle;

a hand-held ratchet comprising a head at an end of an angulated handle;

a motor driven rotary placement and removal tool comprising a head at an end of a straight shank, wherein a free end of the shank is configured to removably couple to a motor driven rotary handpiece;

a hand driven placement and removal tool comprising a head at one end of a handle, said handle further comprising a rotating finger rest at a free end of said handle;

a hand-held spanner comprising a head at an end of a straight handle;

a hand-held spanner comprising a head at an end of an angulated handle; and a hand-held placement tool comprising an external involute spline at an end of a shank, said external involute spline being configured to couple to an internal involute spline of the biocompatible implantable device in the form of a dental implant, the shank further comprising an external hex at a free end, said external hex being configured to removably couple to a ratchet; and a barrier ring disposed between the shank and the external involute spline.

13. The drug delivery system of claim 1, wherein the biocompatible implantable device comprises:

the first closed end being configured to removably couple to the holding device;

the second end being a rounded end;

the hollow body being configured in the form of a hollow cylindrical tube, the inlet in the form of a tubular inlet and configured to removably couple to the first open end of the biocompatible tubing, the tubular inlet comprising threads and the first open end of the biocompatible tubing comprising complimentary threads, the hollow cylindrical tube comprising the plurality of openings in the apical wall, the central lumen forming the flow pathway between said tubular inlet and the plurality of openings in the apical wall;

a barrier ring disposed on an external surface of the hollow body of the biocompatible implantable device between said tubular inlet and the plurality of openings in the apical wall; said barrier ring comprising a convex and smooth first surface facing an overlying soft tissue; a flat and smooth second surface facing an underlying bone; and a plurality of circumferentially disposed holes through said first and second surfaces into which complimentary screws are inserted for securing the biocompatible implantable device to the underlying bone; and threads disposed at a cervical third and a middle third of the external surface of the hollow body of the biocompatible implantable device that extends between the second surface of the circular barrier ring and the second end; wherein when the second part of the hollow body of the biocompatible implantable device is inserted into a complimentary hole formed in the bone and the respiratory mucosa of the maxillary sinus underlying the bone, the apical wall comprising said the plurality of openings is positioned within a lumen of the maxillary sinus cavity; further wherein when an inhalable drug formulation is delivered into the lumen of the maxillary sinus through said biocompatible implantable device, the drug is inhaled from the maxillary sinus during normal inspiration and delivered onto the nasal respiratory mucosa and an olfactory mucosa, whereby the drug is further absorbed into the connective tissue of the nasal respiratory mucosa and the olfactory mucosa, for delivery into the brain through a plurality of routes, said routes being a neural route, a vascular route or a lymphatic route.

14. The drug delivery system of claim 1, wherein the biocompatible implantable device comprises:

the first closed end comprising a projection in the form of an external hexagon configured to removably couple to the holding device;

the second end being a rounded end;

the hollow body being configured in the form of a tapering hollow tube wherein the larger diameter of the hollow body is at the first closed end and the smaller diameter is at the second end of the biocompatible implantable device, further wherein said inlet being an angulated, smooth tubular inlet configured to removably couple to the first open end of the biocompatible tubing; and the central lumen forming the flow pathway between the angulated, smooth tubular inlet and the plurality of openings in the apical wall;

a barrier ring disposed on an external surface of the hollow body of the biocompatible implantable device between the angulated, smooth tubular inlet and the plurality of openings in the apical wall, said barrier ring comprising a flat and smooth first surface configured to face an overlying soft tissue; a flat and smooth second surface configured to face an underlying bone and a plurality of circumferentially disposed holes through said first and second surfaces into which complimentary screws are inserted for securing the biocompatible implantable device to the underlying bone; and threads disposed at a cervical third of the external surface of the hollow body of the biocompatible implantable device that extends between the second surface of the circular barrier ring and the second end; wherein when the second part of the hollow body of the biocompatible implantable device is inserted into a complimentary hole formed in the bone and the respiratory mucosa of the maxillary sinus underlying the bone, the second end and the apical wall of the biocompatible implantable device comprising said plurality of openings are positioned within the lumen of the maxillary sinus cavity; further wherein when the drug is delivered directly into the lumen of the maxillary sinus through the biocompatible implantable device, the maxillary sinus lining epithelial cells move the mucus and said drug through the ostium into the middle meatus and onto the nasal respiratory mucosa resulting in increased retention time on the respiratory mucosal surface and increased absorption of the drug into the underlying connective tissue for further delivery into the brain through a plurality of routes, said plurality of routes being a neural route, a vascular route and a lymphatic route.

15. The drug delivery system of claim 1, wherein the inlet of the biocompatible implantable device is in the form of an opening comprising internal threads.

16. The drug delivery system of claim 1, wherein the biocompatible implantable device comprises a plurality of inlets, and a plurality of flow pathways between said plurality of inlets and the plurality of openings in the apical wall of the biocompatible implantable device.

17. The drug delivery system of claim 1, wherein the biocompatible implantable device comprises at least one flow pathway between the inlet and the at least one of the plurality of opening in the apical wall of the biocompatible implantable device.

18. A method for delivering drugs into the connective tissue of the respiratory mucosa of the maxillary sinus or the nasal cavity using the drug delivery system of claim 1, for delivering the drug into the brain by bypassing the blood brain barrier, comprising:
- elevating a full thickness mucoperiosteal flap at a surgical site over the bone overlying the respiratory mucosa in the maxillary sinus or the nasal cavity region, from a buccal or a palatal region;
- circumscribing a bone window in the bone exposed by the elevating step using a bone trephine drill of appropriate diameter and length slowly rotating the bone trephine drill to pry away the overlying bone without tearing the respiratory mucosa underlying the bone or using a piezo-instrument to remove the bone circumscribed using the bone trephine drill without tearing the respiratory mucosa underlying the bone;
- releasing and elevating the intact respiratory mucosal lining from the surrounding bone margin using a soft tissue elevator of appropriate size and shape;
- placing the biocompatible implantable device of claim 1 of required size into the surgical site using the holding device, wherein the apical wall of the biocompatible implantable device comprising the plurality of openings is placed beneath and in contact with the connective tissue side of the respiratory mucosa;
- connecting the first open end of the biocompatible tubing to the inlet of the biocompatible implantable device and placing the second gen end of the biocompatible tubing that is removably coupled to the cap at a level overlying an oral mucosa in a buccal sulcus, at a buccal gingival sulcus or a palatal gingival sulcus;
- repositioning the mucoperiosteal flap and placing sutures;
- allowing the surgical site to heal;
- after adequate healing, whenever drug delivery to the brain is required, removing the cap removably coupled to the second open end of the biocompatible tubing and connecting the second open end of the biocompatible tubing to the drug infusion source; and
- delivering the drug that can be administered in small quantities without causing any systemic or local complications from the external drug reservoir in a continuous and controlled manner using the external pump at a rate that does not cause backflow of the drug at the surgical site or cause leakage and overflow across the overlying respiratory mucosal lining.

19. The drug delivery method in claim 18, wherein the drug that is delivered into the connective tissue of the overlying respiratory mucosa of the maxillary sinus is further configured for uptake into goblet cells of the maxillary sinus lining epithelium from the underlying connective tissue, wherein when the drug is secreted by the goblet cells along with mucus onto an epithelial surface of the maxillary sinus, said drug is further transported by mucociliary action over a larger epithelial surface of the respiratory mucosa of the maxillary sinus and the nasal cavity resulting in an increased absorption of the drug into the underlying connective tissue of the respiratory mucosa due to the increased retention time of the drug on said epithelial surface of the respiratory mucosa of the maxillary sinus and the nasal cavity; further wherein said absorbed drug is transferred into the brain through a neural route, a vascular route, a counter-current mechanism at the cavernous sinus, inhalation, a lymphatic route or a combination of said routes.

20. The method in claim 18, wherein the second end and the apical wall comprising the plurality of openings of the biocompatible implantable device are placed into the lumen of the maxillary sinus cavity and positioned above the level of the epithelial layer of the respiratory lining mucosa for use in delivering the drug into the brain by bypassing the blood brain barrier, and the method comprising:
- the step of elevating comprises elevating the full thickness mucoperiosteal flap over the bone overlying the respiratory mucosa in the maxillary sinus region, from the buccal or the palatal region;
- the step of circumscribing comprises circumscribing both the bone exposed by the elevating step and the respiratory mucosa underlying the bone being circumscribed;
- removing the circumscribed bone with the bone trephine drill along with the respiratory mucosa underlying the circumscribed bone;
- the step of placing comprises placing the biocompatible implantable device of claim 1 of required size into the surgical site using the holding device such that the apical wall of the biocompatible implantable device comprising the plurality of openings is placed into the maxillary sinus and positioned above the level of the epithelial layer of the respiratory lining mucosa; and
- the step of delivering the drug comprises delivering the drug into the maxillary sinus cavity from the external drug reservoir in a continuous and controlled manner using the external pump, wherein the drug is in the form of an inhalable formulation or can be administered in larger volumes without systemic or local complications.

* * * * *